US006080364A

United States Patent [19]

Mimura et al.

[11] Patent Number: 6,080,364

[45] Date of Patent: Jun. 27, 2000

[54] AUTOMATIC ANALYZER AND SUPPORT SYSTEM THEREFOR

[75] Inventors: Tomonori Mimura, Tomobe-machi; Hiroshi Mitsumaki, Mito; Taku Sakazume; Kazumitsu Kawase, both of Hitachinaka; Atsushi Takahashi, Mito, all of Japan

[73] Assignee: Hitachi, Ltd., Tokyo, Japan

[21] Appl. No.: 09/053,543

[22] Filed: Apr. 2, 1998

[30] Foreign Application Priority Data

Apr. 10, 1997 [JP] Japan .................................... 9-092378

[51] Int. Cl.[7] ...................................................... G01N 35/00

[52] U.S. Cl. ................................ 422/67; 422/63; 422/65; 436/43; 436/47; 436/50

[58] Field of Search ................................ 422/63, 65, 67; 436/43, 47, 50; 364/528.01

[56] References Cited

U.S. PATENT DOCUMENTS 4,678,755 7/1987 Shinohara et al. .

FOREIGN PATENT DOCUMENTS 7-92171 4/1995 Japan .

*Primary Examiner*—Long V. Le

*Attorney, Agent, or Firm*—Beall Law Offices

[57] ABSTRACT

An automatic analyzer has a plurality of analytical units to which analysis items are allocated. When necessity of execution of calibration or accuracy management occurs, a display block relating to an occurrence cause on a state inspection screen flickers. When a receiving button corresponding to the flickering display block is instructed, the related analysis item name and analytical unit name are displayed in the display area and calibration or accuracy management is executed.

7 Claims, 22 Drawing Sheets

COMPUTER
MEMORY
PRINTER
CRT
OPERATOR UNIT
FD
cpu

DISPENSER
60
62
12
PIPETTER
47a
20
48a
19a
15a
14a
65
64
1, 74, 77
46a
5A
66
67
A/D
LOG
31a
30a
COMPUTER
6A
2
17
1
70
78
74
79
77

START
CALIBRATION PRESETTING PROCESS
610
ACCURACY MANAGEMENT PRESETTING PROCESS
620
ANALYSIS MONITOR PROCESS
630
END

CALIBRATION PRESETTING PROCESS
PRESETTING ITEM INPUT RECEPTION
710
THE PRESETTING ITEM IS STORED
720
THE PRESETTING FIELD FLICKERS
730
740
PRESETTING ITEM DISPLAY INSTRUCTED?
NO
YES
THE PRESETTING ITEM IS DISPLAYED
750
A

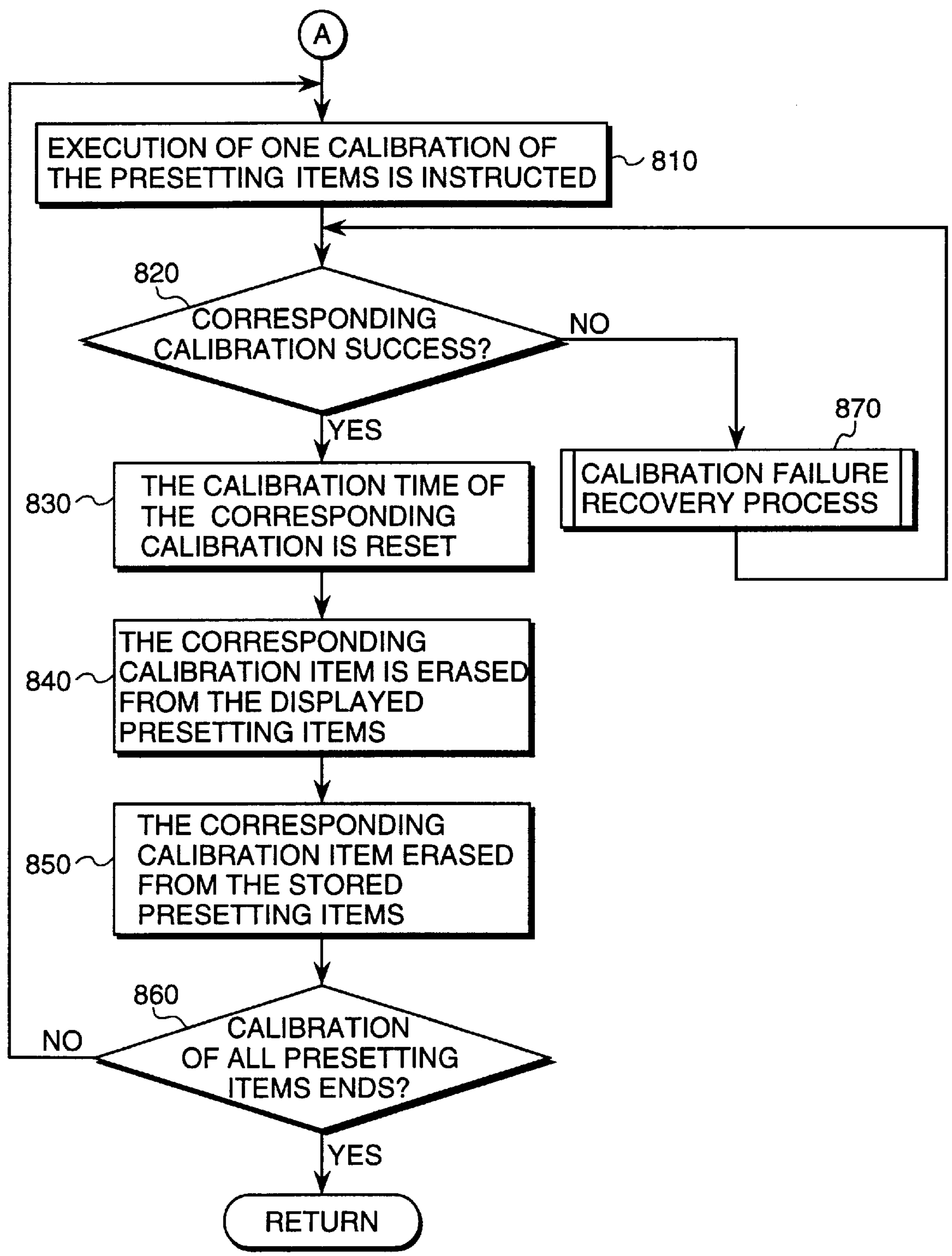
FIG.8
A
EXECUTION OF ONE CALIBRATION OF THE PRESETTING ITEMS IS INSTRUCTED
810
820
CORRESPONDING CALIBRATION SUCCESS?
NO
YES
870
CALIBRATION FAILURE RECOVERY PROCESS
830
THE CALIBRATION TIME OF THE CORRESPONDING CALIBRATION IS RESET
840
THE CORRESPONDING CALIBRATION ITEM IS ERASED FROM THE DISPLAYED PRESETTING ITEMS
850
THE CORRESPONDING CALIBRATION ITEM ERASED FROM THE STORED PRESETTING ITEMS
860
NO
CALIBRATION OF ALL PRESETTING ITEMS ENDS?
YES
RETURN

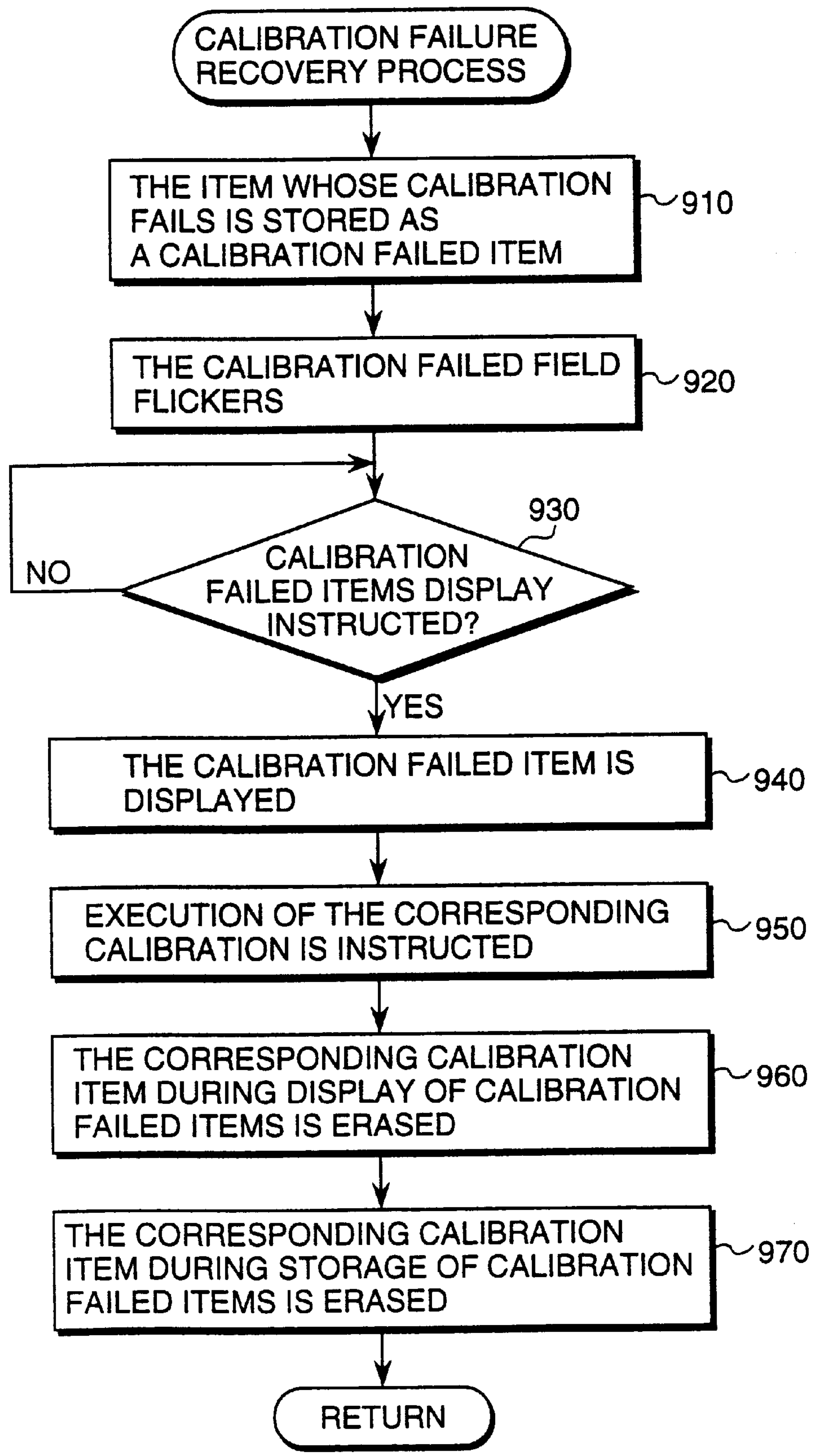
FIG.9
CALIBRATION FAILURE RECOVERY PROCESS
THE ITEM WHOSE CALIBRATION FAILS IS STORED AS A CALIBRATION FAILED ITEM
910
THE CALIBRATION FAILED FIELD FLICKERS
920
930
CALIBRATION FAILED ITEMS DISPLAY INSTRUCTED?
NO
YES
THE CALIBRATION FAILED ITEM IS DISPLAYED
940
EXECUTION OF THE CORRESPONDING CALIBRATION IS INSTRUCTED
950
THE CORRESPONDING CALIBRATION ITEM DURING DISPLAY OF CALIBRATION FAILED ITEMS IS ERASED
960
THE CORRESPONDING CALIBRATION ITEM DURING STORAGE OF CALIBRATION FAILED ITEMS IS ERASED
970
RETURN ACCURACY MANAGEMENT PRESETTING PROCESS
INPUT OF PRESETTING ITEMS IS RECEIVED
1010
THE PRESETTING ITEMS ARE STORED
1020
THE PRESETTING FIELD FLICKERS
1030
1040
PRESETTING ITEM DISPLAY INSTRUCTED?
NO
YES
THE PRESETTING ITEMS ARE DISPLAYED
1050
A'

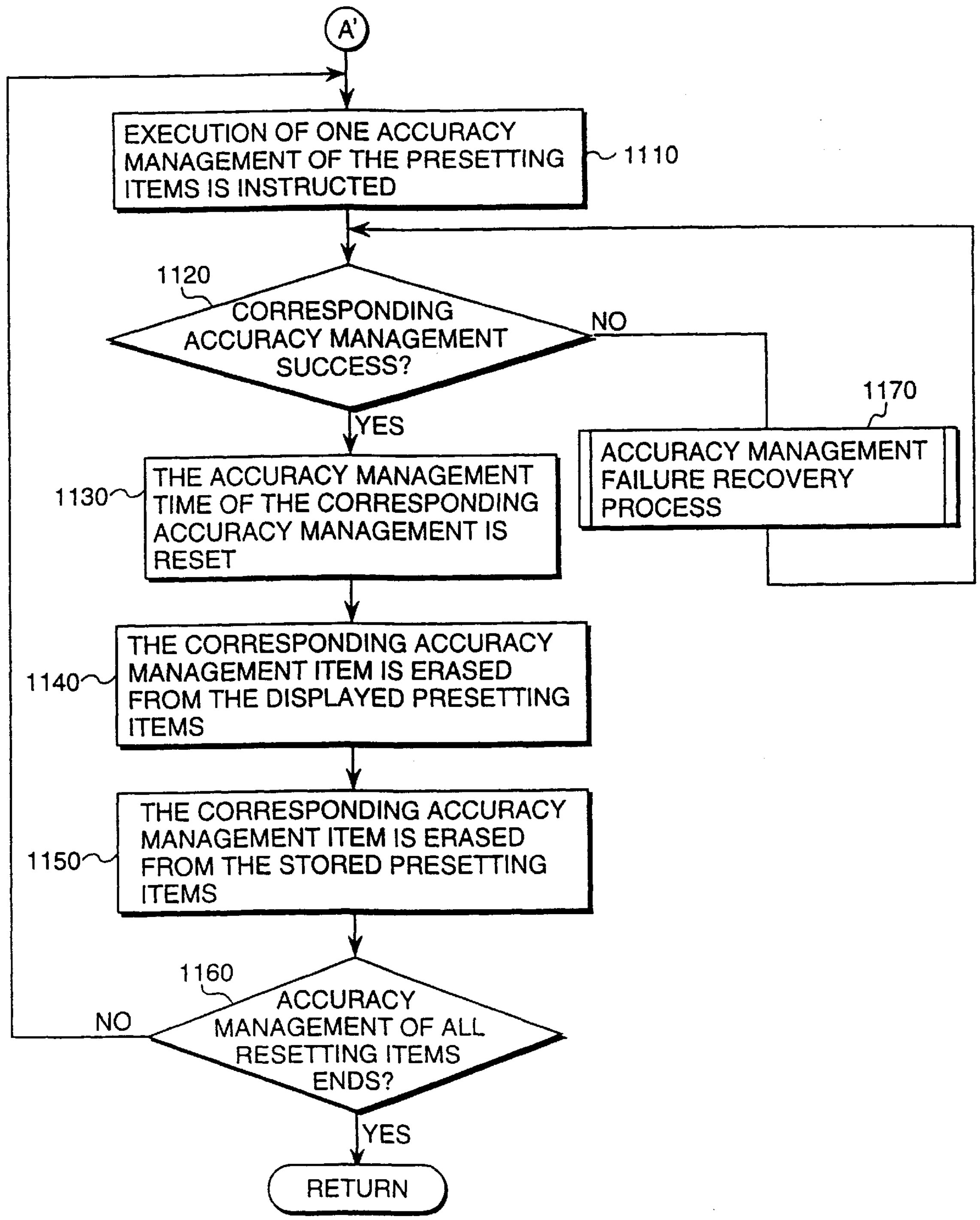
FIG.11
A'
EXECUTION OF ONE ACCURACY MANAGEMENT OF THE PRESETTING ITEMS IS INSTRUCTED
1110
1120
CORRESPONDING ACCURACY MANAGEMENT SUCCESS?
NO
YES
1170
ACCURACY MANAGEMENT FAILURE RECOVERY PROCESS
1130
THE ACCURACY MANAGEMENT TIME OF THE CORRESPONDING ACCURACY MANAGEMENT IS RESET
1140
THE CORRESPONDING ACCURACY MANAGEMENT ITEM IS ERASED FROM THE DISPLAYED PRESETTING ITEMS
1150
THE CORRESPONDING ACCURACY MANAGEMENT ITEM IS ERASED FROM THE STORED PRESETTING ITEMS
1160
ACCURACY MANAGEMENT OF ALL RESETTING ITEMS ENDS?
NO
YES
RETURN

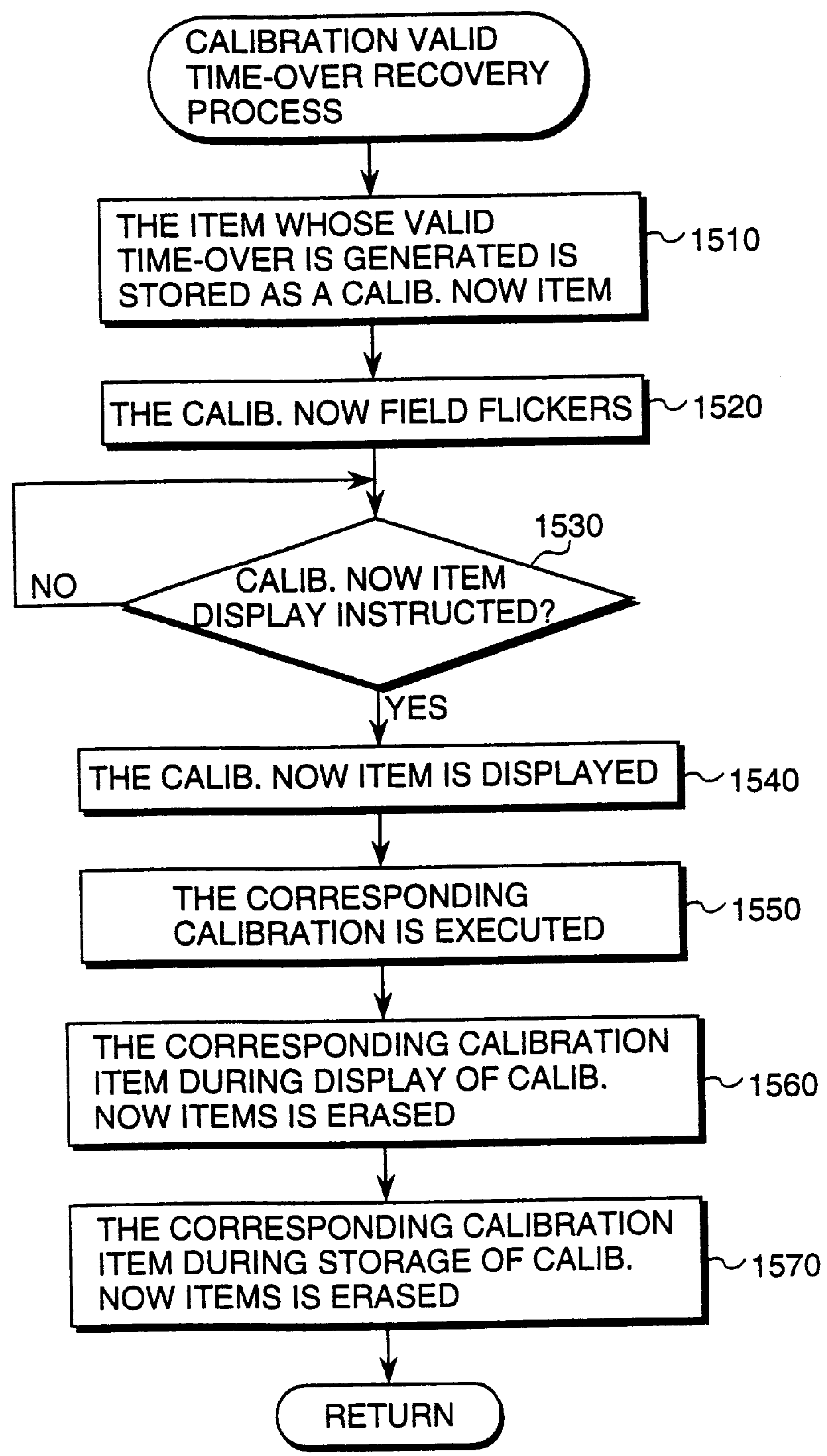
FIG.15
CALIBRATION VALID TIME-OVER RECOVERY PROCESS
THE ITEM WHOSE VALID TIME-OVER IS GENERATED IS STORED AS A CALIB. NOW ITEM
1510
THE CALIB. NOW FIELD FLICKERS
1520
1530
CALIB. NOW ITEM DISPLAY INSTRUCTED?
NO
YES
THE CALIB. NOW ITEM IS DISPLAYED
1540
THE CORRESPONDING CALIBRATION IS EXECUTED
1550
THE CORRESPONDING CALIBRATION ITEM DURING DISPLAY OF CALIB. NOW ITEMS IS ERASED
1560
THE CORRESPONDING CALIBRATION ITEM DURING STORAGE OF CALIB. NOW ITEMS IS ERASED
1570
RETURN

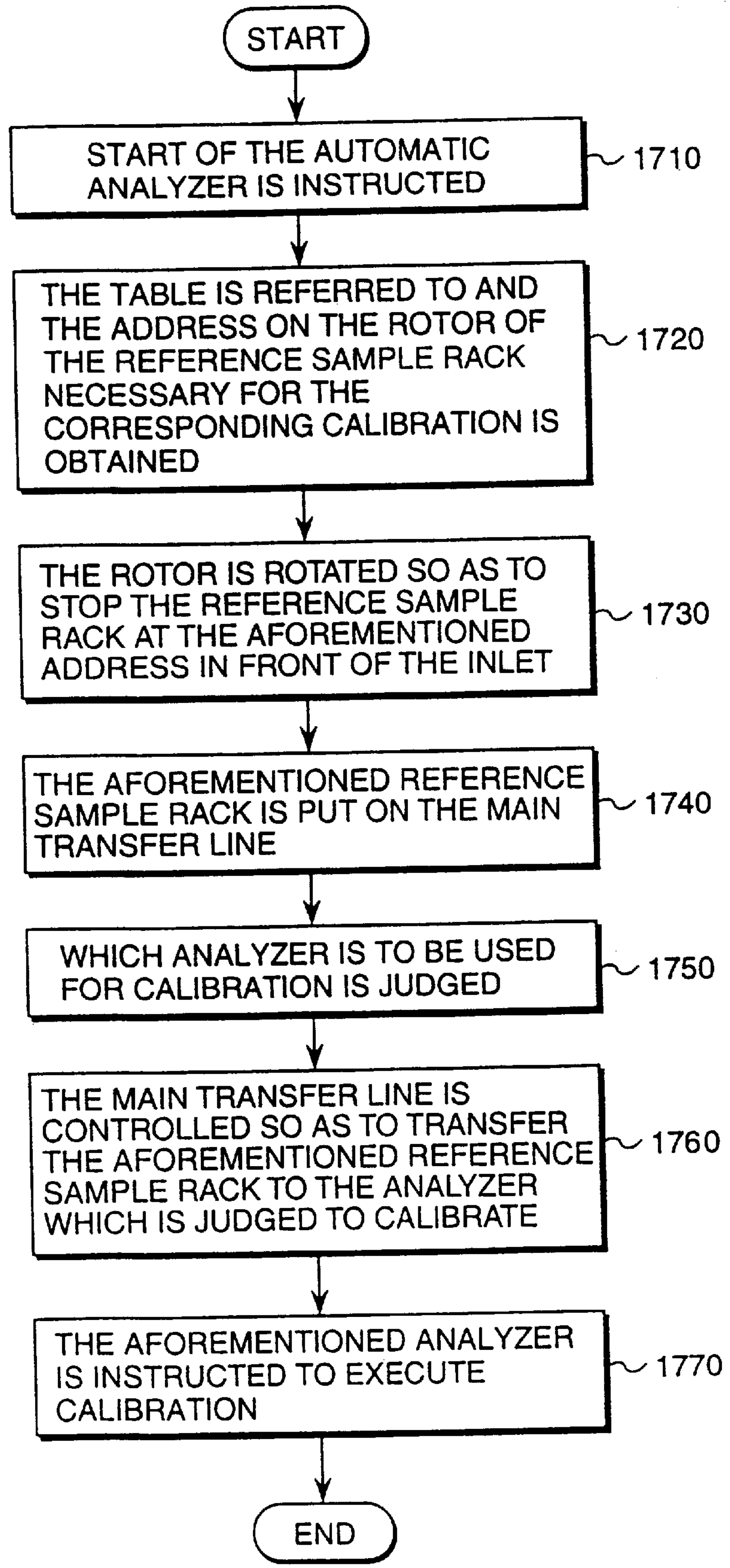
FIG.17
START
START OF THE AUTOMATIC ANALYZER IS INSTRUCTED
1710
THE TABLE IS REFERRED TO AND THE ADDRESS ON THE ROTOR OF THE REFERENCE SAMPLE RACK NECESSARY FOR THE CORRESPONDING CALIBRATION IS OBTAINED
1720
THE ROTOR IS ROTATED SO AS TO STOP THE REFERENCE SAMPLE RACK AT THE AFOREMENTIONED ADDRESS IN FRONT OF THE INLET
1730
THE AFOREMENTIONED REFERENCE SAMPLE RACK IS PUT ON THE MAIN TRANSFER LINE
1740
WHICH ANALYZER IS TO BE USED FOR CALIBRATION IS JUDGED
1750
THE MAIN TRANSFER LINE IS CONTROLLED SO AS TO TRANSFER THE AFOREMENTIONED REFERENCE SAMPLE RACK TO THE ANALYZER WHICH IS JUDGED TO CALIBRATE
1760
THE AFOREMENTIONED ANALYZER IS INSTRUCTED TO EXECUTE CALIBRATION
1770
END

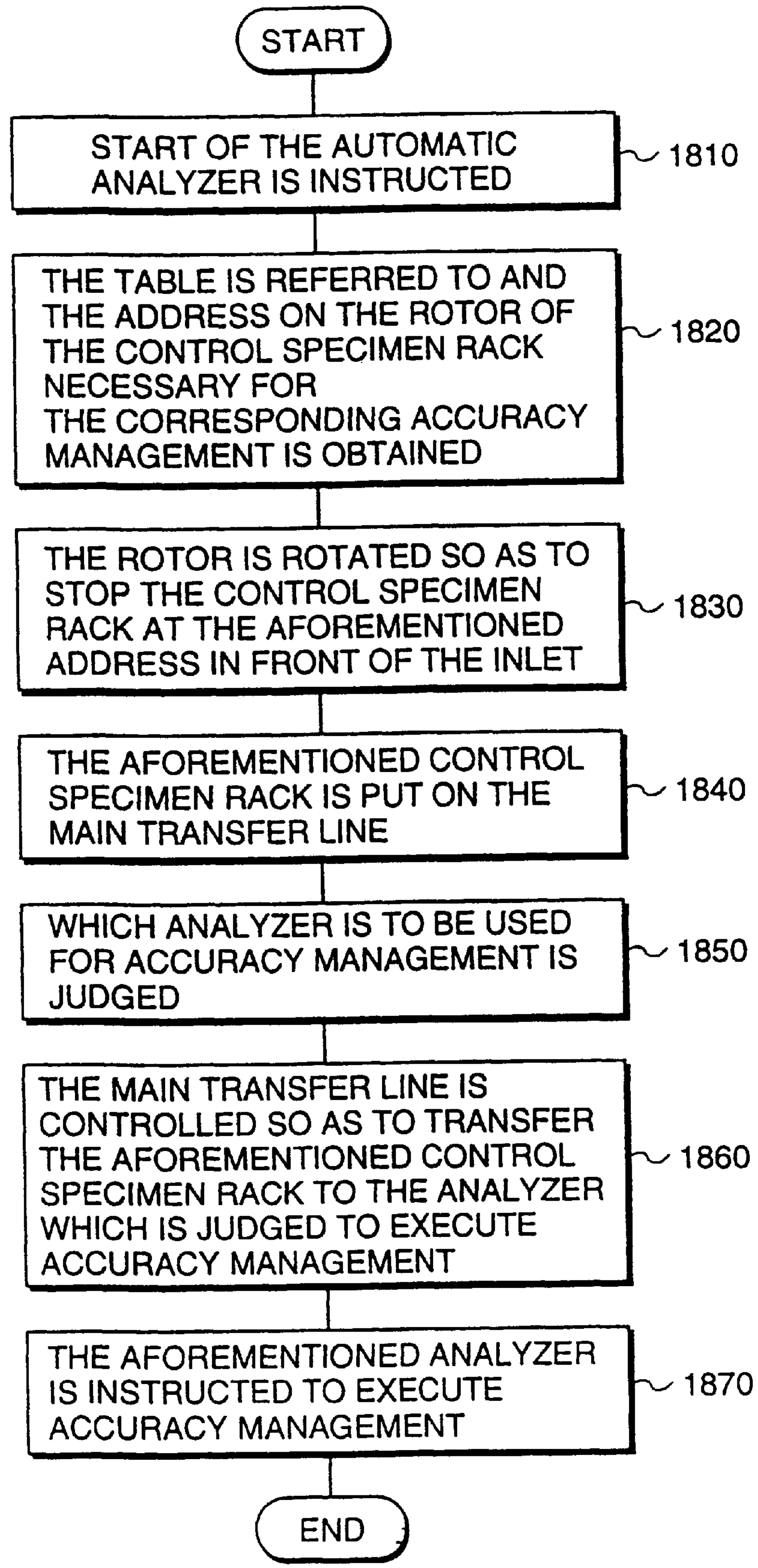
FIG.18
START
START OF THE AUTOMATIC ANALYZER IS INSTRUCTED
1810
THE TABLE IS REFERRED TO AND THE ADDRESS ON THE ROTOR OF THE CONTROL SPECIMEN RACK NECESSARY FOR THE CORRESPONDING ACCURACY MANAGEMENT IS OBTAINED
1820
THE ROTOR IS ROTATED SO AS TO STOP THE CONTROL SPECIMEN RACK AT THE AFOREMENTIONED ADDRESS IN FRONT OF THE INLET
1830
THE AFOREMENTIONED CONTROL SPECIMEN RACK IS PUT ON THE MAIN TRANSFER LINE
1840
WHICH ANALYZER IS TO BE USED FOR ACCURACY MANAGEMENT IS JUDGED
1850
THE MAIN TRANSFER LINE IS CONTROLLED SO AS TO TRANSFER THE AFOREMENTIONED CONTROL SPECIMEN RACK TO THE ANALYZER WHICH IS JUDGED TO EXECUTE ACCURACY MANAGEMENT
1860
THE AFOREMENTIONED ANALYZER IS INSTRUCTED TO EXECUTE ACCURACY MANAGEMENT
1870
END

FIG. 19

DATA STRUCTURE

CALIBRATION INFORMATION

1900

| ITEM AST |
|---|
| CALIBRATION VALID TIME<br>ELAPSED TIME (PREVIOUS EXECUTION TIME)<br>CALIBRATION EXECUTION FORMAT<br>(ONLY BLANK, REFERENCE SAMPLE, ETC.)<br>CALIBRATION PARAMETER<br>CALIBRATION EXECUTION CONDITION<br>(VALID TIME, REAGENT BOTTLE) |

ACCURACY MANAGEMENT INFORMATION

1910

| ITEM AST |
|---|
| ACCURACY MANAGEMENT VALID TIME<br>ELAPSED TIME (PREVIOUS EXECUTION TIME)<br>ACCURACY MANAGEMENT EXECUTION FORMAT<br>(CONTROL SPECIMEN, ETC.)<br>ACCURACY MANAGEMENT EXECUTION CONDITION<br>(VALID TIME, REAGENT BOTTLE) |

FIG.22

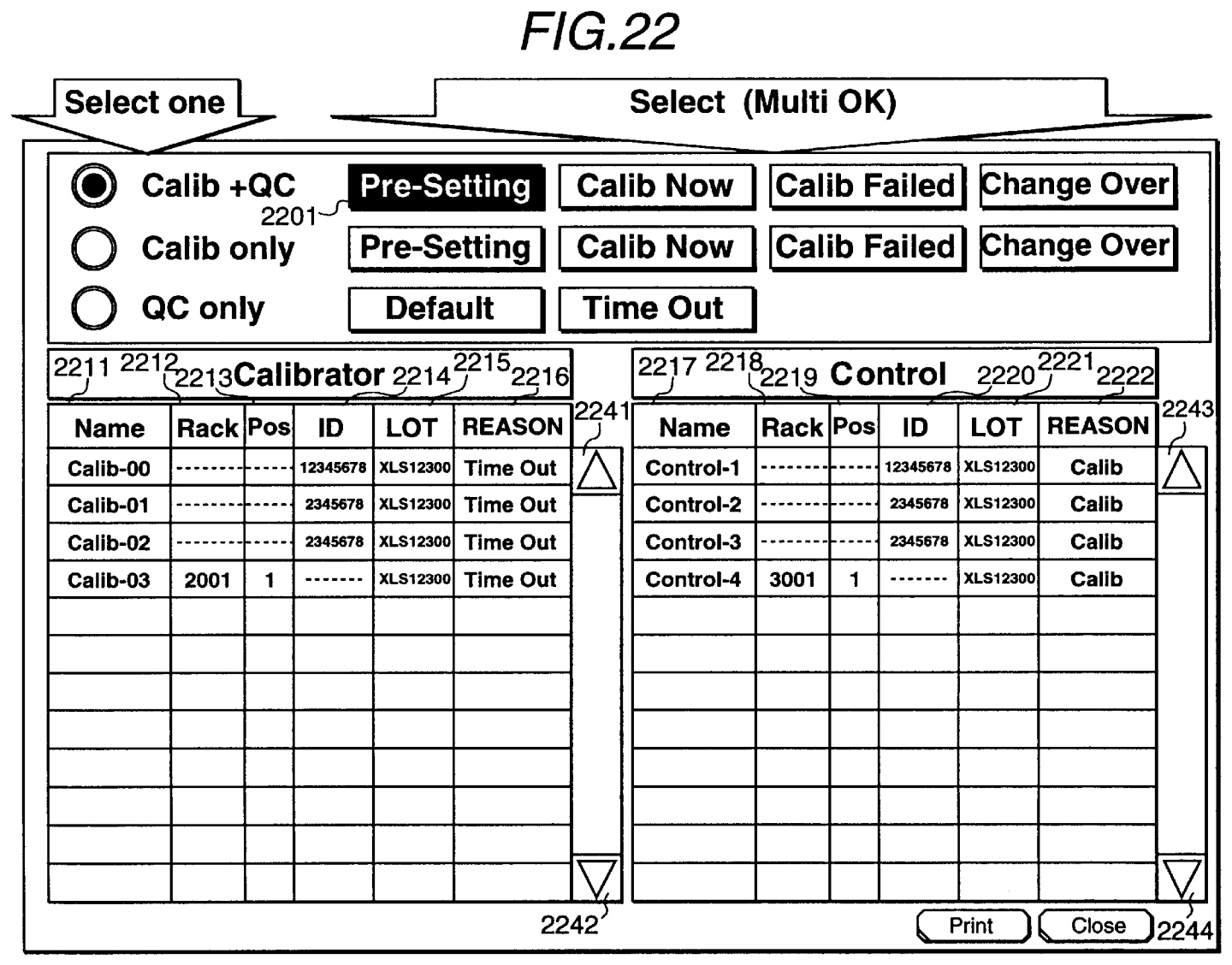

Select one

Select (Multi OK)

Calib +QC | Pre-Setting | Calib Now | Calib Failed | Change Over

2201

Calib only | Pre-Setting | Calib Now | Calib Failed | Change Over

QC only | Default | Time Out 2211 2212 2213 Calibrator 2214 2215 2216

| Name | Rack | Pos | ID | LOT | REASON |
| --- | --- | --- | --- | --- | --- |
| Calib-00 | -------- | ----- | 12345678 | XLS12300 | Time Out |
| Calib-01 | -------- | ----- | 2345678 | XLS12300 | Time Out |
| Calib-02 | -------- | ----- | 2345678 | XLS12300 | Time Out |
| Calib-03 | 2001 | 1 | ------- | XLS12300 | Time Out |

2241 2242

2217 2218 2219 Control 2220 2221 2222

| Name | Rack | Pos | ID | LOT | REASON |
| --- | --- | --- | --- | --- | --- |
| Control-1 | -------- | ----- | 12345678 | XLS12300 | Calib |
| Control-2 | -------- | ----- | 2345678 | XLS12300 | Calib |
| Control-3 | -------- | ----- | 2345678 | XLS12300 | Calib |
| Control-4 | 3001 | 1 | ------- | XLS12300 | Calib |

2243 2244

Print Close

AUTOMATIC ANALYZER AND SUPPORT SYSTEM THEREFOR

BACKGROUND OF THE INVENTION

1. Field of the Invention

The present invention relates to an automatic analyzer for analyzing components of a biological sample and a support system therefor, and relates to effective operation and management of calibration and accuracy management in the automatic analyzer.

2. Description of the Related Art

In an automatic analyzer for analyzing components of a biological sample such as blood or urine using a reagent, it is necessary to execute a calibration which is a calibration curve quality control and accuracy management for keeping the automatic analyzer in the satisfactory state at the beginning of analysis start, or at any predetermined time decided depending on each reagent during analysis, or when necessary during analysis.

Calibration is executed using a reference sample in a concentration predetermined according to each analysis item. Accuracy management is executed using a control sample in the concentration predetermined according to each analysis item. Calibration and accuracy management have a reliable time according to each analysis item respectively. Therefore, when this reliable time elapses, it is necessary to execute calibration or accuracy management once again. If, when calibration or accuracy management is executed, the result is not within the predetermined range, it is decided as a failure and it is necessary to execute calibration or accuracy management once again. Even when a reagent is taken out from a new reagent bottle in each analysis item, it is necessary to execute calibration once again.

U.S. Pat. No. 4,678,755 instructs an automatic chemical analyzer which can execute calibration. This prior art can store the calibration time interval for each analysis item and display alarm data on the display unit by the control means for an analysis item for which the reliable time of a calibration curve elapses. When the calibration menu screen is outputted on the display unit, a list of all analysis items handled by the analyzer is displayed and an alarm symbol is assigned only to analysis items among them for which the reliable time has elapsed.

On the other hand, Japanese Patent Application Laid-Open 7-92171 instructs a transfer system for arranging a plurality of analyzers along the container transfer line and distributing containers in a number according to the analytical capacity of each analyzer sequentially to a plurality of analyzers. However, this prior art describes nothing regarding calibration and accuracy management.

The equipment described in Japanese Patent Application Laid-Open 7-92171 is effective in analysis of many samples, though extremely many analysis item kinds are handled. Therefore, when using an automatic analyzer having a plurality of analytical units in the same way as with that in Japanese Patent Application Laid-Open 7-92171, if the method described in U.S. Pat. No. 4,678,755 is applied as it is, the operation for performing calibration or accuracy management will be complicated.

SUMMARY OF THE INVENTION

An object of the present invention is to provide an automatic analyzer for easily notifying to an operator that necessity of execution of calibration or accuracy management occurs in each of a plurality of analytical units, and allowing each analytical unit to accurately execute calibration or accuracy management, and a support system therefor.

Another object of the present invention is to provide a storage medium storing an operation program for allowing an automatic analyzer to execute calibration or accuracy management.

Still another object of the present invention is to provide an automatic analyzer having a constitution for supplying samples in the known concentration to be used for calibration or accuracy management repeatedly to a plurality of analytical units.

A further object of the present invention is to provide an automatic analyzer operation method for easily executing calibration or accuracy management when efficiently operating a plurality of analytical units in an analyzer.

The automatic analyzer support system on the basis of the present invention is applied to an automatic analyzer in which a plurality of analytical units are arranged along the transfer line. This support system has a display request means for a state inspection screen of calibration or accuracy management, a screen display means for displaying a state inspection screen having a plurality of classification captions installed in correspondence to classification of a plurality of states relating to calibration or accuracy management and an instruction button for instructing display of detailed information corresponding to each classification caption in association with the display request, and a control means for controlling, when an instruction is outputted by the instruction button, so as to display the analysis item name of the corresponding state and the analytical unit name for executing calibration or accuracy management of the corresponding analysis item on the state inspection screen.

In a desirable embodiment of the present invention, when a state corresponding to one of a plurality of classification captions occurs, the display state of the corresponding classification caption is changed. If, when an occurrence of two or more states requiring calibration or accuracy management for the same analysis item is informed by two or more classification captions, the calibration or accuracy management corresponding to one classification caption is executed, and the information by the residual other classification captions is canceled.

The automatic analyzer on the basis of the present invention has a plurality of analytical units arranged along the transfer line for transferring samples, and is structured so that samples stop at the analytical unit selected according to the analysis item via the transfer line. The automatic analyzer includes a specific sample rack for holding specific samples to be measured repeatedly at the predetermined interval, a rack standby unit for allowing the specific sample rack to stand by and sending the specific sample rack toward the transfer line in correspondence to execution of calibration or accuracy management, and a control means for controlling the operation of the transfer line so as to allow the specific sample rack taken out from the predetermined position on the rack standby unit to stop at the analytical unit requiring calibration or accuracy management via the transfer line, and then to return the specific sample rack to the predetermined position on the rack standby unit.

The automatic analyzer operation method on the basis of the present invention is a method for allocating the same specific analysis item to two or more analytical units respectively, receiving an instruction for executing calibration or accuracy management when a state requiring calibration or accuracy management for the automatic analyzer occurs, and executing calibration or accuracy management for the specific analysis item on the basis of the execution instruction by two or more analytical units respectively.

BRIEF DESCRIPTION OF THE DRAWINGS

FIG. 8 is a flow chart showing the calibration presetting process of the support system of the present invention.

FIG. 9 is a flow chart showing the calibration failure recovery process of the support system of the present invention.

FIG. 11 is a flow chart showing the accuracy management presetting process of the support system of the present invention.

FIG. 15 is a flow chart showing the calibration reliable time-over recovery process of the support system of the present invention.

FIG. 17 is a flow chart showing the calibration execution instruction process of the support system of the present invention.

FIG. 18 is a flow chart showing the accuracy management execution instruction process of the support system of the present invention.

FIG. 19 is a drawing for explaining the structure of data to be stored by the support system of the present invention.

FIG. 22 is a drawing for explaining an example of the display screen to be displayed by the support system of the present invention.

DESCRIPTION OF PREFERRED EMBODIMENTS

The embodiments of the present invention will be explained with reference to FIGS. 1 to 22.

Firstly, the constitution of an example of an automatic analyzer to which the present invention is applied will be explained.

Figure 1:
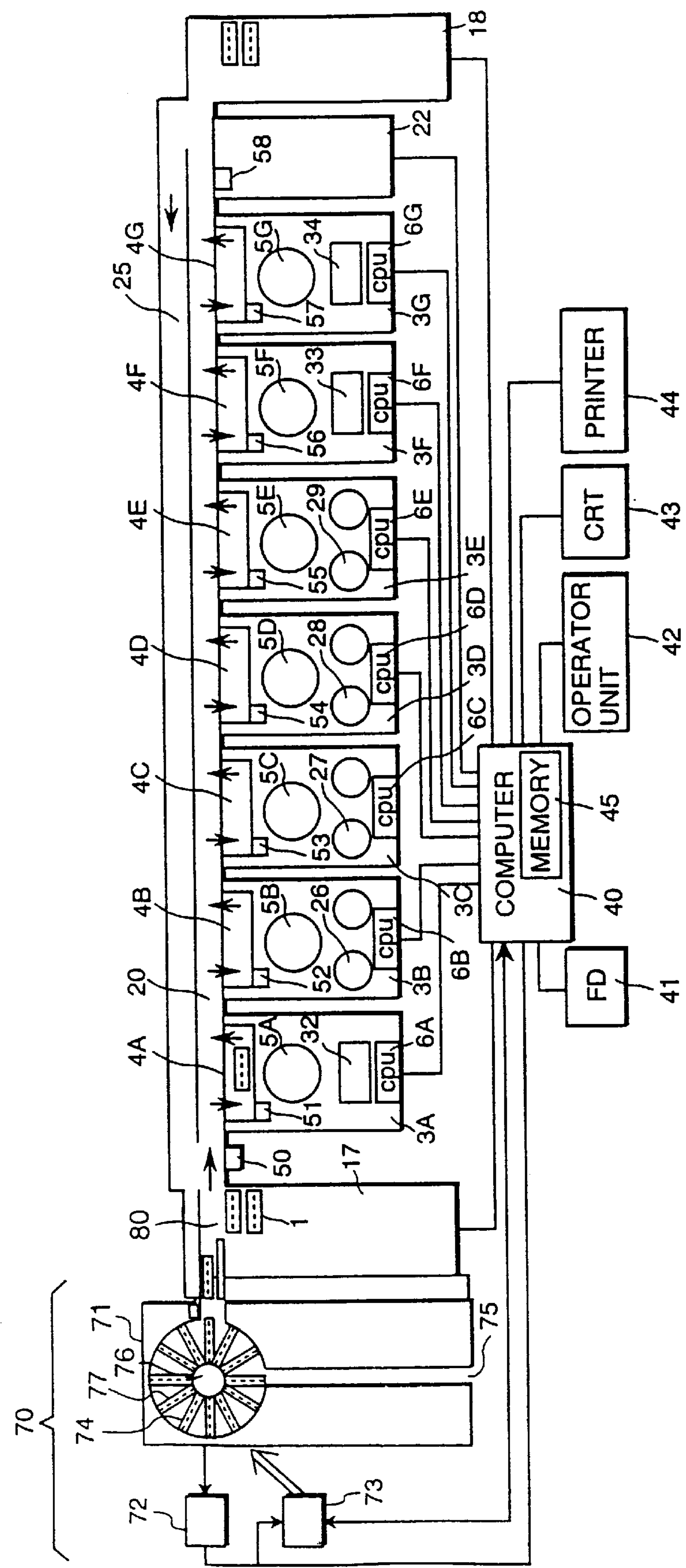
FIG. 1 is a drawing showing a rough constitution of an automatic analyzer of an embodiment of the present invention.
Figure 2:
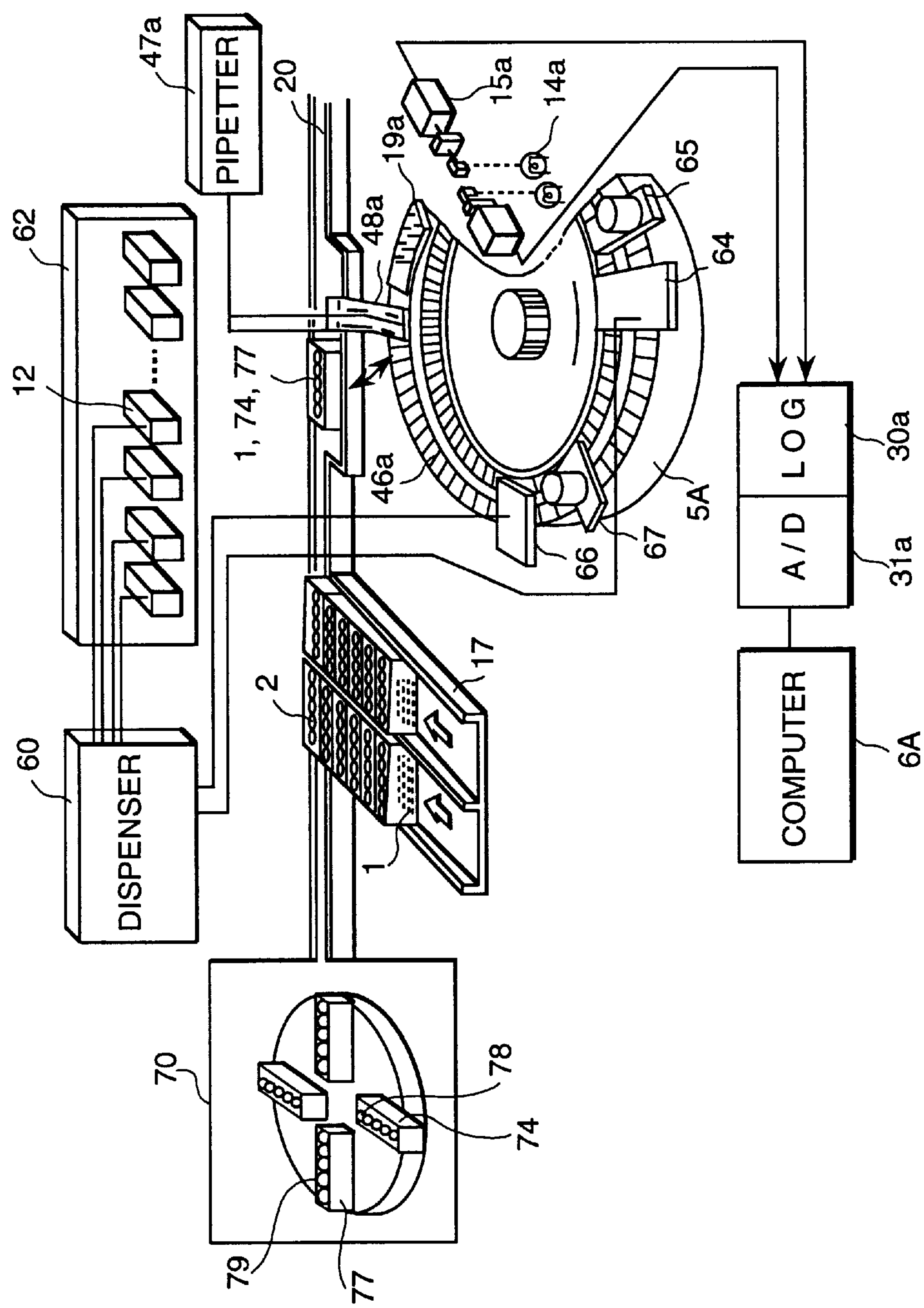
FIG. 2 is a drawing for explaining an example of the analyzer of a dispenser system in the embodiment shown in FIG. 1.
Figure 3:
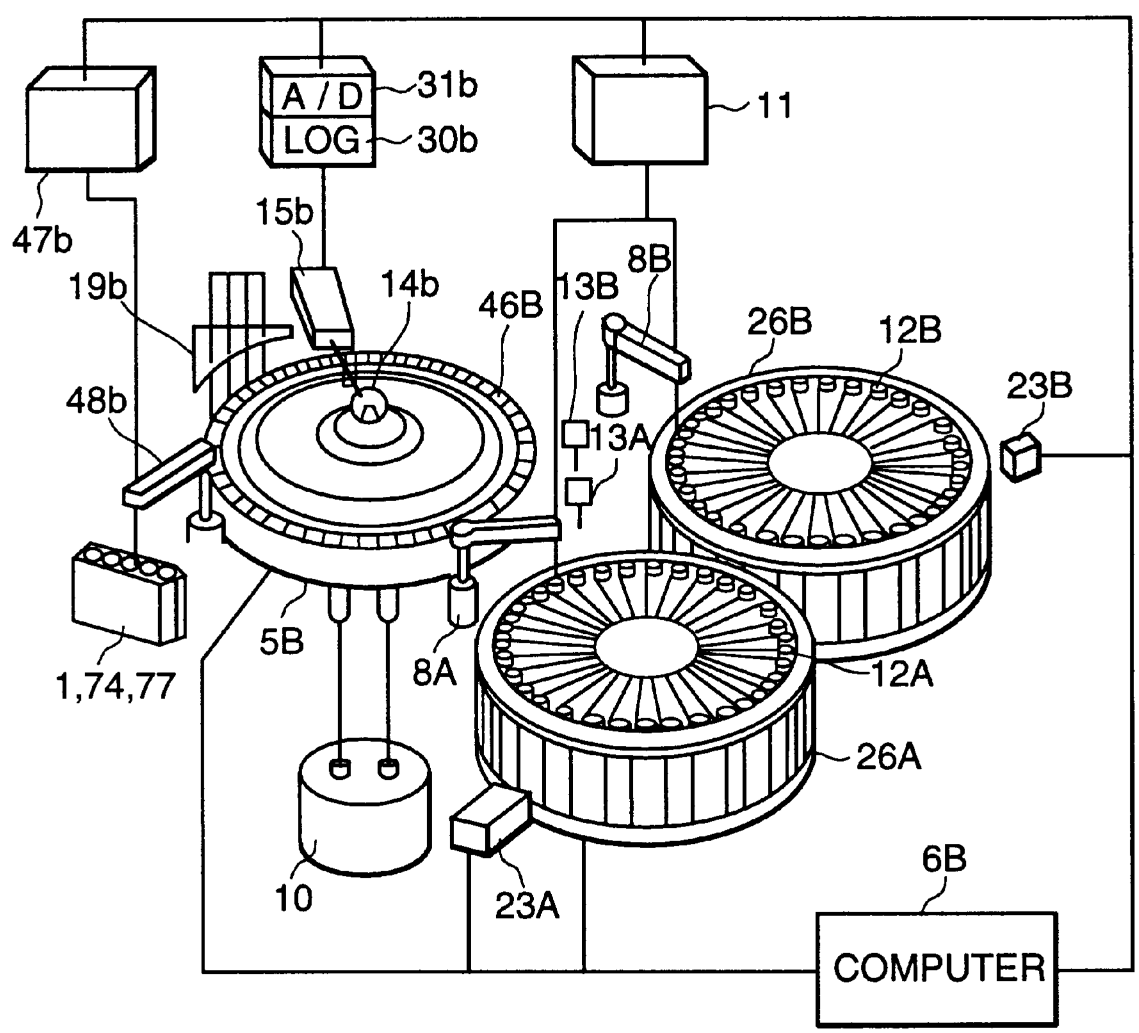
FIG. 3 is a drawing for explaining an example of the analyzer of a pipetter system in the embodiment shown in FIG. 1.

FIG. 1 is a schematic block diagram of an automatic analyzer which can analyze serum, blood plasma, or urine as a biological sample. In the automatic analyzer shown in FIG. 1, an analyzer for supplying a reagent by a dispenser system as shown in FIG. 2 and an analyzer for supplying a reagent by a pipetter system as shown in FIG. 3 coexist. The analyzers 3A, 3F, and 3G shown in FIG. 1 are analyzers of a dispenser system which has a fixed analytical channel and a plurality of reagent discharge nozzles specialized for each reagent. The analyzers 3B, 3C, 3D, and 3E are analyzers of a pipetter system in which the analytical channel is not fixed and accessed at random and a reagent is pipetted according to the analysis item one after another by one reagent pipetting nozzle.

In FIG. 1, the analytical units 3A to 3G for analyzing serum have sampling lines 4A to 4G which are transfer paths having a function for positioning the racks such as patient sample racks 1, reference sample racks 74, and control sample racks 77 which are fetched from a main transfer line 20 at the sampling position and then returning them to the main transfer line 20, identification information readers 51 to 57 installed in correspondence with each sampling line for reading identification information of the racks and identification information of each sample container on the racks, reaction units 5A to 5G for promoting a reaction between a patient sample, or a reference sample, or a control sample and a reagent according to the analysis item in a reaction container and measuring a reaction sample, for example, optically, and a reagent feeder respectively. Reagent feeders 26, 27, 28, and 29 of each analyzer are of a pipetter system and reagent feeders 32, 33, and 34 are of a dispenser system.

A rack sender 17 for patient samples has an area for setting many patient sample racks 1 and a sending mechanism for sending the patient sample racks 1 to the main transfer line 20 one by one. A rack collector 18 has an area for collecting the patient sample racks 1 housing samples analyzed by one analytical unit and an aligning mechanism for arranging the sample racks in order. A temporary storage unit 22 stores the patient sample racks 1 in which samples are sampled by the analyzers temporarily until measured results are outputted, sends the sample racks so as to transfer by the main transfer line 20 once again via a return line 25 when re-examination becomes necessary, and sends the sample racks to the rack collector 18 when re-examination is not necessary.

A standby unit 70 for a specific sample rack to be used repeatedly like a reference sample rack and a control sample rack has an ID identification unit 71 for reading identification information of the reference sample racks 74 and the control sample racks 77 inputted from a rack inlet 75 by an operator, a means for transferring the reference sample racks 74 and the control sample racks 77 whose identification information is read by the rack ID identification unit 71 to a rotor 76, the rotor 76 for holding the reference sample racks 74 and the control sample racks 77 which are transferred, a sensor 72 for detecting the holding positions of the reference sample racks 74 and the control sample racks 77 on the rotor 76, and a drive means 73 for rotating the rotor 76. When execution of calibration is instructed by a total control computer 40, the rotor 76 is rotated by the drive means 73, and the racks 74 housing containers of a reference sample in the known concentration including the analysis item are positioned at a sending path 80, and the reference sample racks 74 pulled out from the predetermined position of the rotor 76 are sent toward the main transfer line 20 via the sending path 80.

The main transfer line 20 allows the reference sample racks 74 to stop selectively at the analytical unit requiring calibration for the analysis item. The sampling mechanism of the corresponding analytical unit pipettes a predetermined amount of reference sample into the reaction container of the analytical unit from the reference sample racks.

When execution of accuracy management is instructed by the whole control computer 40, the rotor 76 is rotated by the drive means 73 in the same way and then the racks 77 housing control samples including the analysis item necessary for execution of the accuracy management are sent so as to be transferred by the main transfer line 20. The reference sample racks 74 finishing sampling for calibration and the control sample racks 77 finishing sampling for accuracy management are transferred to the main transfer line 20 from the sampling lines 4A to 4G of the corresponding analytical unit, then transferred to the standby unit 70 via the return line 25, and housed at the original holding position on the rotor 76. The housed racks 74 and 77 stand by in the rotor 76 until an instruction of calibration or accuracy management is outputted thereafter. The standby unit 70 is kept at a predetermined temperature so as to prevent the reference sample and control samples from degradation. A constitution using the rotor 76 is used here. However, another constitution using a holding means of an elevator type instead of a rotor may be used.

A controller has the whole control computer 40, computers 6A to 6G on the analytical unit side installed in correspondence with each analytical unit, and a floppy disk memory 41 which is an external storage unit of a portable medium type. The computers 6A to 6G on the analytical unit side take partial charge of processing of an output signal from a photometer of each analytical unit. The total control computer 40 connected to those computers 6A to 6G controls the operation of each analytical unit, the operation of the rack transfer system, and the operation of a necessary portion in the system, and executes operations and control which are necessary for various information processes. The partial charge of the role between the computers is not so limited, but can be changed to various conditions according to the necessity of the constitution, or it is also possible to make the computers on the analytical unit side unnecessary using only the total control computer 40. The total control computer 40 is equipped with a storage part 45, and an operator console 42 for data input, a CRT 43 which is a display unit for displaying information on the screen, and a printer 44 for outputting measured results are connected to it. As a storage part 45, for example, a built-in hard disk can be used.

A program is installed in each computer beforehand. Each computer executes processes such as control according to the installed program. The program is supplied, for example, in the state that it is stored in a storage medium such as a floppy disk, CD-ROM, and others. As a program, in addition to the control program for executing analysis, the program for supporting the operation of analysis of the present invention and others are installed.

The patient sample rack 1, for example, as shown in the example of FIG. 2, comprises a box-shaped container retainer in which a plurality of, for example, five patient sample containers 2 housing patient samples are loaded. However, various shapes other than this shape can be used. The reference sample racks 74 and the control sample racks 77, for example, as shown in the example of FIG. 2, also comprise a box-shaped container retainer in which a plurality of, for example, five reference sample containers 78 housing a reference sample or five control sample containers 79 housing control samples are loaded respectively. However, various shapes other than this shape can be used. On the outer walls of the patient sample racks 1, the reference sample racks 74, and the control sample racks 77, an identification information medium showing rack identification information is installed respectively and on the outer walls of the patient sample containers 2, the reference sample containers 78, or the control sample containers 79, an identification information medium showing inner solution identification information is installed respectively. As these identification information media, bar code labels or magnetic recording media are used. Each bar code label installed on the patient sample racks 1, the reference sample racks 74, and the control sample racks 77 has the rack number and sample kind information. Each bar code installed on the patient sample containers 2 has information regarding each sample, for example, the reception number, reception year, month, and day, patient name, patient number, sample kind, and sample request analysis item. The reference sample containers 78 or the control sample containers 79 have information regarding each reference sample or control sample, for example, the reference sample name or control sample name, ID, and manufacturing lot number.

An identification information reader 50 shown in FIG. 1 inputs read results of the identification information (bar code) of a rack and sample container before transfer by the main transfer line 20 to the computer 40. An identification information reader 58 installed in the temporary storage unit 22 transfers, when a rack enters or comes out from the temporary storage unit 22, the bar codes of the rack and sample container to the total computer 40. In this case, the rack means the patient sample rack 1, the reference sample rack 74, or the control sample rack 77. In this case, the sample container means the sample container 2, the reference sample container 78, or the control sample container 79.

On reagent bottles 12, 12A, and 12B for various analysis items to be housed in the reagent feeders of the analytical units 3A to 3G, reagent identification information is displayed on their outer walls by bar codes. Reagent identification information has the reagent manufacturing lot number, reagent bottle size, usable reagent amount, reliable term, sequence number different for each bottle, and analysis item code. Such reagent identification information is read by a bar code reader and is associated with each of the analytical units 3A to 3G, and the setting position of each reagent bottle in the reagent feeder, the maximum number of analyses of the reagent calculated from the usable sample amount and the amount of one pipetting, the kind of analysis item, and the analytical unit number housing the reagent are registered in the storage part 45.

The main transfer line 20 is equipped with the patient sample racks 1, a transfer belt on which the reference sample racks 74 or the control sample racks 77 are loaded, and a belt drive motor (both are not shown in the drawing, and is controlled by the controller so as to continuously transfer the patient sample racks 1 and the reference sample racks 74 or the control sample racks 77 to the desired position. The sampling lines 4A to 4G can transfer the transfer belt intermittently so as to stop the racks at the rack pull-in position, pipetting position, and rack sending position. The patient sample racks 1 and the reference sample racks 74 or the control sample racks 77 to be transferred by the main transfer line 20 are transferred along the line of analytical units, stopped in front of the analytical unit specified by the controller, and transferred to the rack pull-in position of the sampling line by a rack transfer mechanism (not shown in the drawing) immediately. They are pipetted by a pipetter which will be described later at the pipetting position. The patient sample racks 1 and the reference sample racks 74 or the control sample racks 77 for which the pipetting operation ends are transferred onto the main transfer line 20 from the rack sending position of the sampling line by the rack transfer mechanism. As a rack transfer mechanism, a transfer robot having a rack holding arm or a mechanism having a push lever for pushing racks from one of the main transfer line and the sampling line to the other is used.

A constitution example of an analytical unit of the dispenser system will be explained by referring to FIG. 2. The reaction unit 5A of the analytical unit 3A has two reaction container lines having light transmissible reaction containers 46*a* and concentrically arranged, and a multi-wavelength photometer 15*a* for separating light transmitted through the reaction containers 46*a* from a light source 14*a* for each reaction container line and receiving a plurality of wave lengths. So as to act on each reaction container line, in the neighborhood of the reaction unit 5A, a pipetter 48*a* having a pipette nozzle connected to a sample pipetter pump 47*a*, a first reagent nozzle group retainer 64 and a second reagent nozzle group retainer 66 which are connected to a reagent dispenser pump 60, a first stirrer 65, a second stirrer 67, and a reaction container cleaning mechanism 19*a* are arranged. In a reagent refrigerator 62, reagent bottles 12 of a first reagent and a second reagent (only for necessary analysis items) are arranged and cooled to a predetermined temperature. A reagent sample in each reagent bottle 12 is supplied to the corresponding reagent discharge nozzle on the reaction container line from the reagent dispenser pump 60 via a tube. In this case, a dispenser system reagent feeder 32 of the analytical unit 3A shown in FIG. 1 includes the reagent dispenser pump 60 shown in FIG. 2, the reagent refrigerator 62 having many reagent bottles 12, the first reagent nozzle group retainer 64, and the second reagent nozzle group retainer 66.

Each patient sample rack 1 supplied from the rack sender 17 is transferred by the main transfer line 20 and moved to the sampling line 4A of the analyzer 3A when an analysis process by the analytical unit 3A is necessary. For a patient sample on the patient sample rack 1 reaching the pipetting position, a predetermined amount is pipetted into the reaction container 46*a* by the pipette nozzle of the pipetter 48*a*. Into this reaction container 46*a*, the reagent corresponding to the analysis item is discharged at the predetermined position on the reaction container line and the reaction proceeds. After a lapse of the predetermined time, the optical characteristics of the reaction sample in the reaction container 46*a* are measured by the multi-wavelength photometer 15*a*. A signal outputted from the multi-wavelength photometer 15*a* is subjected to the processing of a logarithm converter 30*a* and an analog-digital converter 31*a* under the control by the computer 6A on the analytical unit side and sent to the total control computer 40.

Each reference sample rack 74 supplied from the standby unit 70 is transferred by the main transfer line 20 and moved to the sampling line 4A of the analytical unit 3A when calibration of the analytical unit 3A is necessary. In this case, calibration means an operation for measuring a sample (reference sample) of a known concentration and creating a calibration curve.

For the reference sample on the reference sample rack 74 reaching the pipetting position, a predetermined amount is pipetted into the reaction container 46*a* by the pipette nozzle of the pipetter 48*a*. Into this reaction container 46*a*, the reagent corresponding to the analysis item is discharged at the predetermined position on the reaction container line and the reaction proceeds. After a lapse of the predetermined time, the optical characteristics of the reaction sample in the reaction container 46*a* are measured by the multi-wavelength photometer 15*a*.

A signal outputted from the multi-wavelength photometer 15*a* is subjected to the processing of the logarithm converter 30*a* and the analog-digital converter 31*a* under the control by the computer 6A on the analytical unit side. On the basis of this data, a formula of calibration curve is obtained and a calibration curve is created by the computer 6A, success or failure of the calibration is decided, and the success or failure is sent to the total control computer 40. In this case, success of calibration means that a calibration curve is created and the created calibration curve is not deviated greatly from the past calibration curve obtained empirically. Failure of calibration means that a calibration curve is not created or the created calibration curve is greatly deviated from the past calibration curve obtained empirically. The computer 6A on the analytical unit side is provided with data of a calibration curve empirically obtained in the past and data regarding the deviation tolerance, and decides success or failure of calibration on the basis of this data.

It is also possible that the computer 6A on the analytical unit side does not decide success or failure of calibration, but sends information regarding the obtained formula of calibration curve to the total control computer 40, and the total control computer 40 is provided with data of a calibration curve empirically obtained in the past and data regarding the deviation tolerance and decides success or failure of calibration on the basis of this data.

Each control sample rack 77 supplied from the standby unit 70 is transferred by the main transfer line 20 and moved to the sampling line 4A of the analytical unit 3A when accuracy management of the analytical unit 3A is necessary. In this case, accuracy management means an operation for measuring a sample (control sample) of a known concentration, decides whether the measured result is within the predetermined range, and then checks whether the automatic analyzer and reagent are in a satisfactory state.

For the control sample on the control sample rack 77 reaching the pipetting position, a predetermined amount is pipetted into the reaction container 46*a* by the pipette nozzle of the pipetter 48*a*. Into this reaction container 46*a*, the reagent corresponding to the analysis item is discharged at the predetermined position on the reaction container line and the reaction proceeds. After a lapse of a predetermined time, the optical characteristics of the reaction sample in the reaction container 46*a* are measured by the multi-wavelength photometer 15*a*.

A signal outputted from the multi-wavelength photometer 15*a* is subjected to the processing of the logarithm converter 30*a* and the analog-digital converter 31*a* under the control by the computer 6A on the analytical unit side. On the basis of this data, success or failure of the accuracy management is decided by the computer 6A on the analytical unit side. In this case, success of accuracy management means the status that accuracy is measured and the measured accuracy is kept at a predetermined accuracy. Failure of accuracy management means the status that accuracy is not measured or the measured accuracy is not kept at the predetermined accuracy. The decided success or failure of accuracy management is sent to the total control computer 40.

It is also possible that the computer 6A on the analytical unit side does not decide success or failure of accuracy management, but sends only information as to whether measurement can be made or not and information of measured values when measurement can be made to the total control computer 40, and the total control computer 40 decides success or failure of accuracy management.

The analytical units 3F and 3G of the dispenser system also have the same constitution as that of the analytical unit 3A.

Next, a constitution example of an analytical unit of the pipetter system will be explained by referring to FIG. 3. In the reaction containers 46*b* arranged in the reaction unit 5B of the analytical unit 3B, the reaction of a sample and reagent regarding the predetermined analysis item proceeds. The patient sample racks 1 moved to the sampling line B (FIG. 1) from the main transfer line 20 are positioned at the pipetting position, the instructed sample is sampled by the pipette nozzle of the pipetter 48*b*, and a predetermined amount of sample is discharged to the reaction containers 46*b*. The pipetter 48*b* has a pipetter pump 47*b*. The reaction unit 5B is kept at a constant temperature (for example, 37° C.) by a constant temperature sample supplied from a constant temperature oven 10.

The pipetter system reagent feeder 26 of the analytical unit shown in FIG. 3 has two reagent disks 26A and 26B for the first reagent and the second reagent. For the reagent bottles 12A and 12B containing various reagents prepared for many kinds of analysis items, reagent identification information is displayed on their outer walls by bar codes. When the reagent bottles 12A and 12B are loaded on the reagent disks 26A and 26B, the reagent identification information of the reagent bottles are read by bar code readers 23A and 23B and the information is registered in the storage part 45 together with the set positions of the reagent bottles on the reagent disks, the corresponding analysis items, and the analytical unit numbers where the reagent bottles are set. Reagent pipetters 8A and 8B have reagent pipetter pumps 11 connected to the pipette nozzles which can swing and move up and down.

The line of the reaction container 46*b* in which the patient sample is pipetted is rotated and moved, and a predetermined amount of reagent sample is sucked into the reaction container by the reagent pipetter 8A from the reagent bottle 12A positioned at the reagent suction position according to the kind of analysis item. The first reagent is discharged into the reaction container 46*b* at the reagent addition position. The content is stirred by a stirring mechanism 13A at the stirring position, and then the reaction container line is moved several times. When the reaction container 46*b* reaches the second reagent addition position, the reagent pipetter 8B sucks the reagent sample from the reagent bottle 12B positioned at the reagent suction position according to the analysis item and discharges the reagent into the reaction container. Then, the content of the reaction container is stirred by a stirring mechanism 13B. Thereafter, accompanying rotation and transfer of the reaction container line, the reaction container 46*b* passes luminous flux from a light source 14*b* and light transmitted through the reaction sample of the reaction container 46*b* is detected by a multi-wavelength photometer 15*b*.

A signal with the wave length corresponding to the analysis item is processed by a logarithm converter 30*b* and an analog-digital converter 31*b* which are controlled by the computer 6B on the analytical unit side, and the digital signal is sent to the total control computer 40. The measured reaction container 46*b* is cleaned by a cleaning mechanism 19*b* and used once again.

When calibration of the analytical unit 3B is necessary, the reference sample racks 74 are moved to the sampling line 4B of the analytical unit 3B. The reference sample racks 74 are positioned at the pipetting position, the instructed reference sample is sampled by the pipette nozzle of the pipetter 48*b*, and a predetermined amount of reference sample is discharged to the reaction containers 46*b*. The reaction of this reference sample proceeds in the same way as the reaction of the aforementioned patient sample. A signal with the wave length of the reaction sample is processed by the logarithm converter 30*b* and the analog-digital converter 31*b* which are controlled by the computer 6B on the analytical unit side. On the basis of this data, a formula of calibration curve is obtained and a calibration curve is created by the computer 6B on the analytical unit side, success or failure of the calibration is decided, and the success or failure is sent to the total control computer 40. The computer 6B on the analytical unit side is provided with data of a calibration curve empirically obtained in the past and data regarding the deviation tolerance, and decides success or failure of calibration on the basis of this data.

It is also possible that the computer 6B on the analytical unit side does not decide success or failure of calibration, but sends information regarding the obtained formula of calibration curve to the total control computer 40, and the total control computer 40 is provided with data of a calibration curve empirically obtained in the past and data regarding the deviation tolerance and decides success or failure of calibration on the basis of this data.

When accuracy management of the analytical unit 3B is necessary, the control sample racks 77 are moved to the sampling line 4B of the analytical unit 3B. The control sample racks 77 are positioned at the pipetting position, the instructed control sample is sampled by the pipette nozzle of the pipetter 48*b*, and a predetermined amount of control sample is discharged to the reaction containers 46*b*. The reaction of this control sample proceeds in the same way as the reaction of the aforementioned patient sample.

A signal with the wave length of the reaction sample is processed by the logarithm converter 30*b* and the analog-digital converter 31*b* which are controlled by the computer 6B on the analytical unit side. On the basis of this data, whether the predetermined accuracy is kept in the computer 6A on the analytical unit side is decided and the result is sent to the total control computer 40.

It is also possible that the computer 6A on the analytical unit side does not decide whether the predetermined accuracy is kept, but sends only the measured values to the total control computer 40 and the total control computer 40 decides whether the predetermined accuracy is kept.

The analytical units 3C, 3D, and 3E have the same constitution as that of the analytical unit 3B.

Next, the operation of the equipment of the embodiment shown in FIG. 1 will be explained.

Before the sample racks 1 are set in the rack sender 17 and before the reference sample racks 74 and the control sample racks 77 are set in the standby unit 70, the analysis item for which an examination instruction is requested for each sample from a request source is registered in the total control computer 40 from the operator console 42 together with each sample number beforehand. The analytical condition information of each analysis item, information on calibration, and information on accuracy management are stored on the floppy disk memory 41. The analytical condition information to be shared by a plurality of analytical units when the same analysis item is allocated to two or more analytical units includes a reagent to be used, a wave length to be measured by a photometer, a sample sampling amount, and others.

Information on calibration includes the calibration time interval, calibration execution format (reference sample to be used or calibrator), calibration curve creating method, information on the calibration curve tolerance, calibration execution conditions (in what case calibration is to be executed), and others. Information on accuracy management includes the accuracy management time interval, accuracy management execution format (control sample to be used), calibration curve creating method, information on the accuracy management tolerance, accuracy management execution conditions (in what case accuracy management is to be executed), and others. Among them, the calibration curve creating method, information on the calibration curve tolerance, and information on the accuracy management tolerance are also stored in a storage means (not shown in the drawing) of the computers 6A to 6G on the analytical unit side.

Among the analytical condition information, information stored in correspondence with each reagent bottle includes the necessary number of reagents from the first reagent to the fourth reagent, the code of each reagent bottle in a 5-digit numeral, the pipetting amount of each reagent, the number of tests capable of analysis per each reagent bottle, and others.

When reagent bottles are housed in the reagent feeders 26 to 29 and 32 to 34 of the analytical units 3A to 3G, the reagent identification information of each reagent bottle is associated with the analytical unit number and registered in the total control computer 40. In this case, in a plurality of analyzers of the same group handling the same sample kind, a reagent for the same kind of analysis item is housed. In this case, it is assumed that a serum sample is handled by all the analytical units 3A to 3G. Among them, in the reagent feeder 32 of the analytical unit 3A, for example, the reagent bottles for GOT and GPT which are liver function examination items having a large number of sample requests, and calcium, UA, and BUN which are emergency examination items are housed. In the reagent feeder 26 of the analytical unit 3B, for example, the reagent bottles for GOT and GPT which are liver function examination items and other analysis items having a small number of examination requests are housed. In the reagent feeder 27 of the analytical unit 3C, for example, the reagent bottles for calcium, UA, and BUN which are emergency examination items and other analysis items having a small number of examination requests are housed. Therefore, the liver function examination items can be analyzed by the two analytical units 3A and 3B. The emergency examination items can be analyzed by the two analytical units 3A and 3C. Housing a reagent for what analysis item duplicatedly in how many analytical units is decided by an operator according to the actual situation of the examination room of each institution.

When the reagent bottles 12, 12A, and 12B are housed in the reagent feeders, the reagent identification information installed in each reagent bottle is read, the information which is already registered as analytical condition information is searched using each reagent bottle code as a key, and the analysis item corresponding to the reagent bottle, the bottle size, the number of tests capable of analysis, and the reagent bottle set position are correlated with each other and registered in the total control computer 40. At the same time, the maximum analyzable count on the basis of the total number of reagent bottles for the same kind of analysis item in a plurality of analytical units which can analyze the same kind of analysis item is also registered and displayed on the CRT 43 when necessary. When a corresponding reagent for an analysis item necessary for each analytical unit is housed, before an analysis of a sample, for each analytical unit, calibration for all analysis items which can be analyzed by the analytical unit is executed. The computer on the analytical unit side decides success or failure of the calibration. When the same analysis item is allocated to two or more analytical units respectively, the same reference sample stops at the analytical units and is sampled respectively.

When the execution of calibration ends in success, the success of calibration and the formula of calibration curve obtained as a result of calibration are stored in the storage part 45 of the total control computer 40. The calibration result is used in a concentration operation when the corresponding analysis item is analyzed by each analytical unit.

When the execution of calibration ends in failure, the computer on the analytical unit Side sends the failure of calibration to the total control computer 40. The total control computer 40 displays the failure of calibration on the calibration support screen (this will be described later) of the CRT 43. On the calibration support screen, a button is displayed as an area for inputting an instruction of displaying information of the analysis item for which the calibration fails and when an operator inputs a display instruction of the button via the operator console 42, the information on the failed analysis item is displayed and the process for re-execution of the failed calibration is started.

When the execution of calibration for analysis items in all the analytical units ends in success, for each analytical unit, accuracy management for all analysis items which can be analyzed by the analytical unit is executed. The computer on the analytical side decides success or failure of the accuracy management and sends the decided success or failure to the total control computer 40.

When the execution of accuracy management ends in failure, the whole control computer 40 displays the failure of accuracy management on the accuracy management support screen (this will be described later) of the CRT 43. On the accuracy management support screen, a button is displayed as an area for inputting an instruction of displaying information of the analysis item for which the accuracy management fails, and when an operator inputs a display instruction of the button via the operator console 42, the information on the failed analysis item is displayed and the failed accuracy management is re-executed.

When the execution of accuracy management in all the analytical units ends in success, for each analytical unit, the analysis of an analysis item which can be analyzed by the analytical unit is started.

When the analysis is started, one of the detection racks 1 loaded on the rack sender 17 is pressed out toward the main transfer line 20 and then the identification information of the sample rack 1 or the identification information of the sample container 2 is read by the identification information reader 50. On the basis of the read information, the sample kind on the sample rack 1 is decided by the total control computer 40, the analytical unit group in which conditions are set beforehand for the sample kind is selected, and one analytical unit of the analytical unit group is decided as a sample transfer destination by the later decision result. In this case, it is assumed that for example, a serum sample is decided and a group of the analytical units 3A, 3B, and 3C to which the sample rack is to be transferred is selected.

Furthermore, when the sample identification information is read, the registration situation of sample numbers and analysis items is checked, the analysis item whose measurement is instructed for each sample on the sample rack 1 is decided, and whether each analysis item of each sample is to be analyzed by one of the analytical units 3A, 3B, and 3C is decided by the total control computer 40. In this case, the total control computer 40 monitors the number of analysis items whose analysis is already instructed for each analytical unit and the degree of time required until pipetting end of the samples. Particularly, regarding a specific analysis item which can be analyzed by a plurality of analytical units, which analytical unit can analyze the analysis item efficiently is decided. For example, regarding GOT and GPT which are specific analysis items, which one of the analytical units 3A and 3B has a smallest number of samples waiting for processing at that point of time is decided and one having a shorter waiting time is selected as a specified analytical unit.

In addition to such a method for automatically specifying an analytical unit for analyzing a specific analysis item according to the busy degree of a plurality of analytical units, a specification method for inputting the priority of analytical units to be used for processing of each analysis item beforehand from the operator console 42 by an operator is also possible.

The sample racks 1 having a sample for which a specific analysis item is to be analyzed and a decided transfer destination (for example, the analytical unit 3B) respectively are continuously transferred to the specified analytical unit 3B by the main transfer line 20 and stopped in front of the inlet to the sampling line 4B of the analytical unit 3B. Next, the sample racks 1 are moved to the sampling line 4B and returned to the main transfer line 20 after the predetermined sample is pipetted into the reaction unit 5B by the sample pipetter 48*b* at the pipetting position. When an analysis item to be analyzed by the analytical unit 3C remains in the sample on a sample rack 1, the sample rack 1 is transferred up to the analytical unit 3C by the main transfer line 20 and moved to the sampling line 4C, and the sample is pipetted.

The residual reagent amount in the reagent bottle for each analysis item in each analytical unit is monitored by the total control computer 40. The residual reagent amount monitoring method may be based on detection of the reagent sample level in the reagent bottle when the reagent is pipetted by a sample level detector installed on the reagent pipette nozzle, or on subtracting the analyzable count which is inputted beforehand whenever the reagent is pipetted. For either method, whether the reagent amount for the analysis item is insufficient or not is judged by decision of whether the residual analyzable count reaches the predetermined value or not by the total control computer 40. The predetermined value in this case is set to a small count such as a residual count of 0, 1, or 2.

Furthermore, for example, when it is judged that the GOT reagent of the specified analytical unit 3B is insufficient, the analysis of GOT by the analytical unit 3B is stopped and the analytical unit switching operation is controlled so that the GOT analysis by the analytical unit 3A having a sufficient remainder of GOT reagent is made possible at the same time. Therefore, a sample for which GOT is to be analyzed thereafter is transferred to another analytical unit 3A assigned the next priority, and GOT is analyzed.

The controller in the embodiment shown in FIG. 1 understands to which analytical unit the analysis, calibration, and accuracy management of each analysis item are instructed, and the data is stored in the storage part 45. The total control computer 40 stores the information on which analytical unit processes the analysis, calibration, and accuracy management of each analysis item in the memory table and allows the CRT 43 to display the information when requested by an operator.

In the equipment in the embodiment shown in FIG. 1, the start or stop of each operation of the analytical units 3A to 3G can be instructed by key operation of the operator console 42, and on the basis of such instruction information from the operator console, the total control computer 40 allows the main transfer line 20 to transfer the sample racks 1 from the rack sender 17 only to the residual analytical units except for the analytical unit whose operation is stopped. Particularly, in the time zone that fewer samples are requested and examination work of emergency samples is mainly performed like at night, the equipment can be operated so that, for example, only a minimum amount of analytical units are put into the operation state and the residual analytical units are stopped. In the time zone that the number of request samples is increased, a plurality of analytical units which are stopped are operated.

Furthermore, in the equipment in the embodiment shown in FIG. 1, when an abnormal situation occurs in either analytical unit and the analysis by the analytical unit becomes impossible, so as to let another analytical unit take over the same analysis, the controller instructs transfer of the sample rack to another analytical unit and analysis by another analytical unit. For example, when reagents for a plurality of analysis items are duplicatedly set in the two analytical units 3B and 3C, the analysis can be performed without suspending the analytical operation for a plurality of analysis items.

During analysis by the automatic analyzers as mentioned above, it is necessary to perform calibration and accuracy management at every predetermined time interval for each analysis item, or every the predetermined number of samples. Even when the reagent in a reagent bottle is consumed and a reagent bottle is added, it may be necessary to perform calibration for the reagent in the added reagent bottle.

The automatic analyzer support system of the present invention is a support system for performing calibration and accuracy management before analysis by the automatic analyzers as mentioned above or during analysis by the automatic analyzers, and this support system will be explained hereunder.

Firstly, the calibration support screen displayed on the CRT 43 of the automatic analyzers will be explained. This support screen functions as an inspection screen for the calibration state.

Figure 4:
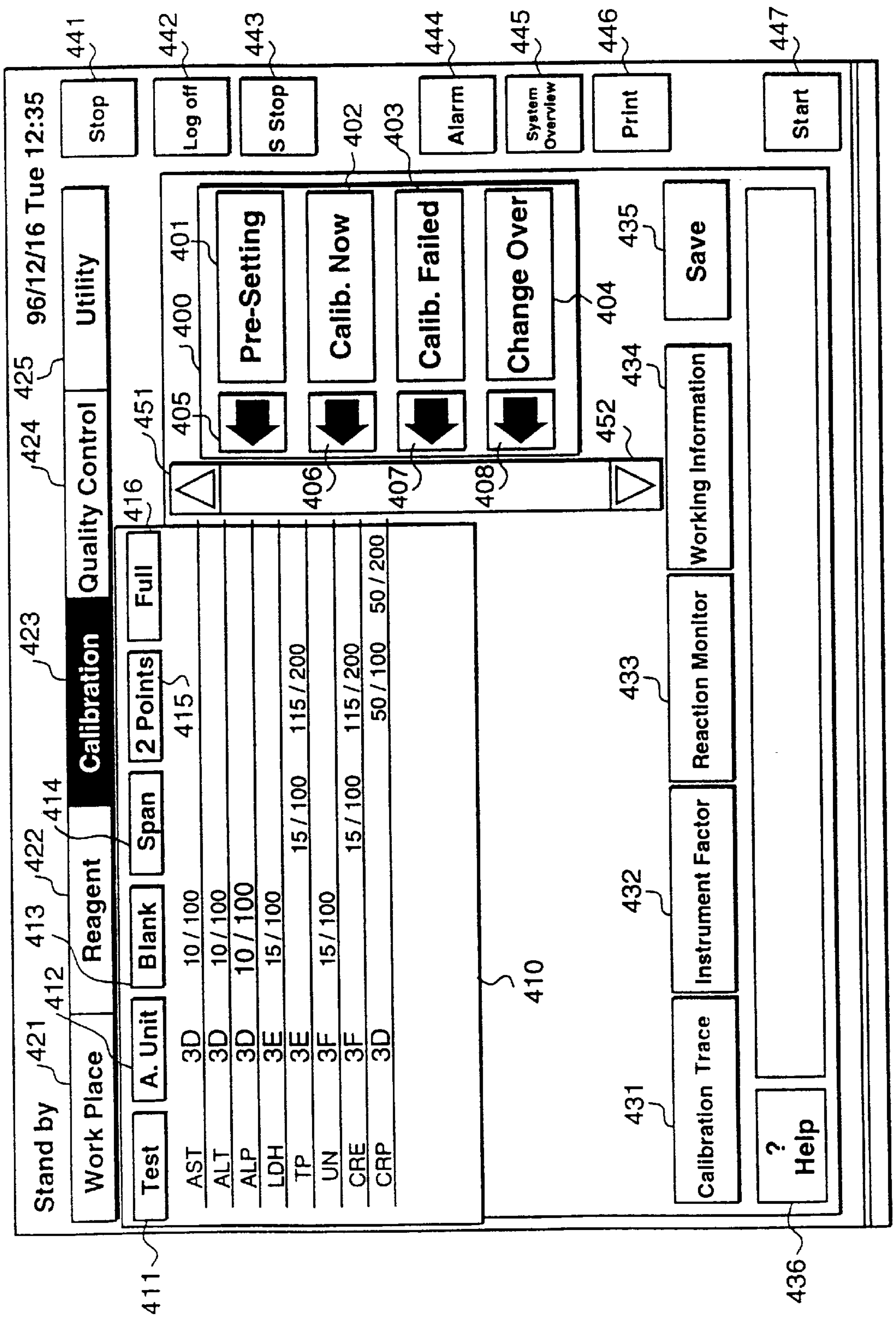
FIG. 4 is a drawing for explaining the calibration tone support screen of the present invention.

FIG. 4 shows an example of the aforementioned calibration support screen. When the Calibration button 423, which is a button in which display and input of the screen are integrated, is instructed by an operator, the display of the Calibration button 423 is reversed and the calibration support screen is displayed at the same time. On this screen, the display portions as an inspection screen for the calibration state are the portions including a display area 400 and a display area 410, and these display areas will be explained first.

At the point of time that the Calibration button 423 is instructed by an operator and the calibration support screen is displayed, nothing is displayed in the display area 410. On the calibration support screen, data is displayed in the areas other than the display area 410.

In the display area 400, display blocks 401 to 404, which are a plurality of indexes classifying and symbolizing a plurality of classification captions installed in correspondence to classification of a plurality of states of calibration (that is the status of the analyzers), are displayed. Furthermore, in the display area 400, instruction buttons or receiving buttons 405 to 408 which are installed in correspondence with these display blocks and receive a display instruction are displayed. When the analyzer status includes the event symbolized by the corresponding display block, the display state of each of the display blocks 401 to 404 as a classification caption is changed.

The Pre-Setting display block 401 in the display area 400 flickers when the analysis item corresponding to the calibration which is to be performed stationarily, such as calibration to be performed before analysis by the automatic analyzers, is registered. If, when the Pre-Setting display block 401 flickers, an operator instructs the button 405, in the display area 410, the analysis item name of the calibration to be performed stationarily is displayed and the calibration of the displayed analysis item is started at the same time.

The Calib. Now display block 402 in the display area 400 flickers when there is an analysis item whose calibration time interval has elapsed. If, when the Calib. Now display block 402 flickers, an operator instructs the button 406, in the display area 410, the corresponding analysis item name is displayed and the calibration of the displayed analysis item is started at the same time.

The Calib. Failed display block 403 in the display area 400 flickers when there is an analysis item in which a failure of calibration occurs. If, when the Calib. Failed display block 403 flickers, an operator instructs the button 407, in the display area 410, the corresponding analysis item name is displayed and the calibration of the displayed analysis item is started at the same time.

The Change Over display block 404 in the display area 400 flickers when there is an analysis item in which the necessity of calibration accompanying addition of a reagent bottle occurs. If, when the Change Over display block 404 flickers, an operator instructs the button 408, in the display area 410, the analysis item name to which a new reagent is added is displayed and the calibration of the displayed analysis item is started at the same time.

Next, the contents to be displayed in the display area 410 will be explained. In the field of Test 411, the analysis item name for which calibration is to be performed is displayed. In the field of A. Unit 412, the analytical unit name for which calibration is to be performed is displayed. In the field of Blank 413, when the calibration to be performed is calibration using a reference sample in one kind of concentration of 0, elapsed time/calibration interval (reliable time) is displayed. In the field of Span 414, when the calibration to be performed is calibration using a reference sample in a known concentration other than one kind of a concentration of 0, elapsed time/calibration interval (reliable time) is displayed. In the field of 2 Points 415, when the calibration to be performed is calibration using a reference sample in two kinds of known concentrations, elapsed time/calibration interval (reliable time) is displayed. In the field of Full 416, when the calibration to be performed is calibration using a reference sample in three or more kinds of known concentrations, elapsed time/calibration interval (reliable time) is displayed.

In FIG. 4, it is necessary to perform calibration of the analysis items AST, ALT, and ALP by the analytical unit 3D using a reference sample in one kind of concentration of 0 and it is displayed that elapsed time/calibration interval is 10/100 for AST, ALT, and ALP. It is also necessary to perform calibration of the analysis item LDH by the analytical unit 3E using a reference sample in one kind of concentration of 0 and it is displayed that elapsed time/calibration interval is 15/100. Furthermore, it is necessary to perform calibration of the analysis item TP by the analytical unit 3E using a reference sample in a known concentration other than one kind of concentration of 0 or a reference sample in two kinds of known concentrations, and it is displayed that elapsed time/calibration interval is 15/100 when a reference sample in a known concentration other than one kind of concentration of 0 is used and 115/200 when a reference sample in two kinds of known concentrations is used. Furthermore, it is also necessary to perform calibration of the analysis item UN by the analytical unit 3F using a reference sample in one kind of concentration of 0 and it is displayed that elapsed time/calibration interval is 15/100. Furthermore, it is necessary to perform calibration of the analysis item CRE by the analytical unit 3F using a reference sample in a known concentration other than one kind of concentration of 0 or a reference sample in two kinds of known concentrations, and it is displayed that elapsed time/calibration interval is 15/100 when a reference sample in a known concentration other than one kind of concentration of 0 is used and 115/200 when a reference sample in two kinds of known concentrations is used. Furthermore, it is necessary to perform calibration of the analysis item CRP by the analytical unit 3D using a reference sample in two kinds of known concentrations or a reference sample in three or more kinds of known concentrations, and it is displayed that elapsed time/calibration interval is 50/100 when a reference sample in two kinds of known concentrations is used and 50/200 when a reference sample in three or more kinds of known concentrations is used.

It is also possible that one of the buttons 405 to 408 is instructed, a list of analysis items in the corresponding state is displayed in the display area 410, and the information on a reference sample necessary for calibration of each analysis item is associated with each analysis item and outputted from the printer 44 at the same time.

When there are many analysis items displayed in the display area 410 and all of them cannot be displayed at one time, it is possible to display the analysis items by scrolling the display area 410 by the button 451 or 452.

Next, the buttons other than the above which are displayed on the calibration support screen will be explained. When the Work Place button 421 is instructed by an operator, the function screen will be displayed. When the Reagent button 422 is instructed by an operator, the reagent bottle management screen will be displayed. When the Quality Control button 424 is instructed by an operator, the accuracy management support screen (this will be described later) will be displayed. When the Utility button 425 is instructed by an operator, the system setting screen for performing the basic setting for moving the equipment will be displayed. When the Calibration Trace button 431 is instructed by an operator, the history of calibration performed in the past will be displayed. When the Instrument Factor button 432 is instructed by an operator, the factor for correcting deviation of each analytical unit will be displayed. When the Reaction Monitor button 433 is instructed by an operator, the data for checking the reaction status of each analysis item will be displayed. When the Working Information button 434 is instructed by an operator, the detailed information of calibration results will be displayed.

When the Save button 435 is instructed by an operator, the list displayed on the screen will be saved. When the Help button 436 is instructed by an operator, the help information will be displayed.

The Stop button 441 is a button for stopping the automatic analyzers. The Log off button 442 is a button for exiting from the display screen. The S.Stop button 443 is a button for stopping sampling and the Alarm button 444 is a button for informing of an error in the equipment. The System Overview button 445 is a button for displaying the movement status of racks so as to inform that the racks flow normally. The Print button 446 is a button for instructing printing and the Start button 447 is a button for starting the automatic analyzers.

Next, the accuracy management support screen displayed on the CRT 43 of the automatic analyzers by this support system will be explained. This support screen functions as an inspection screen for the accuracy management state.

Figure 5:
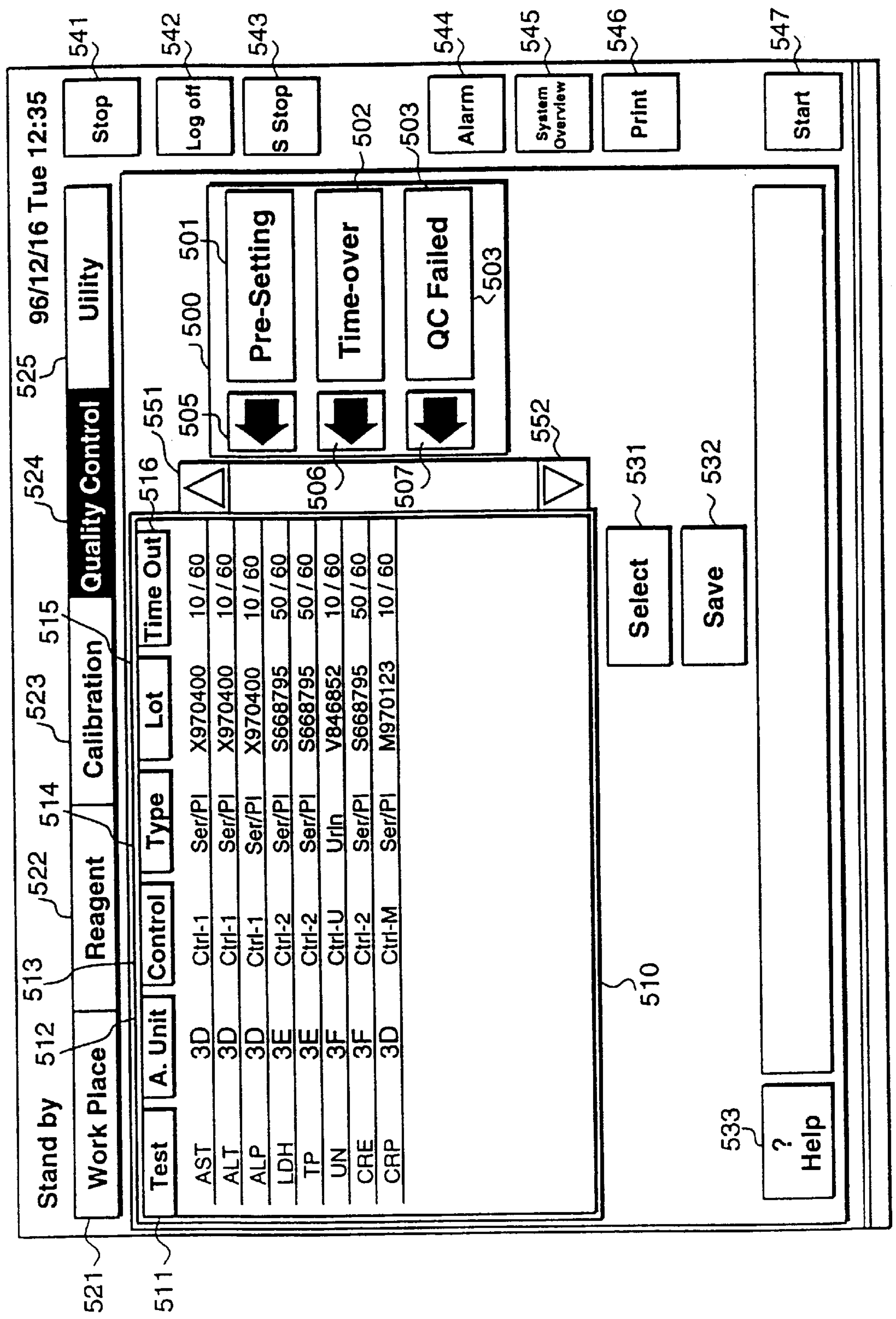
FIG. 5 is a drawing for explaining the accuracy management support screen of the present invention.

FIG. 5 shows an example of the aforementioned accuracy management support screen. When the Quality Control button 524, which is a button in which display and input of the screen are integrated, is instructed by an operator, the display of the Quality Control button 524 is reversed and the accuracy management support screen is displayed at the same time. On this screen, the display portions as an inspection screen for the accuracy management state are the portions including a display area 500 and a display area 510, and these display areas will be explained first.

At the point of time that the Quality Control button 524 is instructed by an operator and the accuracy management support screen is displayed, nothing is displayed in the display area 510. On the accuracy management support screen, data is displayed in the areas other than the display area 510.

In the display area 500, display blocks 501 to 503, which are a plurality of indexes classifying and symbolizing a plurality of classification captions installed in correspondence to classification of a plurality of states of accuracy management (that is, the status of the analyzers), are displayed and furthermore, instruction buttons or receiving buttons 505 to 507, which are installed in correspondence with these display blocks and receive a display instruction, are displayed. When the analyzer status includes the event symbolized by the corresponding display block, the display state of each of the display blocks 401 to 404 as a classification caption is changed.

The Pre-Setting display block 501 in the display area 500 flickers when the analysis item corresponding to the accuracy management which is to be performed stationarily, such as calibration to be performed before analysis by the automatic analyzers, is registered. If, when the Pre-Setting display block 501 flickers, an operator instructs the button 505, in the display area 510, the analysis item of the accuracy management to be performed stationarily is displayed and the accuracy management of the displayed analysis item is started at the same time.

The Time-over display block 502 in the display area 500 flickers when the reliable time of accuracy management elapses. If, when the Time-over display block 502 flickers, an operator instructs the button 506, in the display area 510, the analysis item of the accuracy management to be performed is displayed and the accuracy management of the displayed analysis item is started at the same time.

The QC Failed display block 503 in the display area 500 flickers when a failure of accuracy management occurs. If, when the QC Failed display block 503 flickers, an operator instructs the button 507, in the display area 510, the analysis item of the accuracy management to be performed is displayed and the accuracy management of the displayed analysis item is started at the same time.

Next, the contents to be displayed in the display area 510 will be explained. In the field of Test 511, the analysis item for which accuracy management is to be performed is displayed. In the field of A. Unit 512, the name of the analytical unit for which accuracy management is to be performed is displayed. In the field of Control 513, the name of the control sample to be used for the accuracy management to be performed is displayed. In the field of Type 514, the type for specifying the concentration kind of the control sample to be used for the accuracy management to be performed is displayed. In the field of Lot 515, the manufacturing lot number of the control sample to be used for the accuracy management to be performed is displayed. In the field of Time Out 516, elapsed time/accuracy management interval (reliable time) of the accuracy management to be performed is displayed.

In FIG. 5, it is necessary to perform accuracy management of the analysis items AST, ALT, and ALP by the analytical unit 3D using a control sample of a lot number of X970400 with a name of Ctrl-1 and a type of Ser/P1, and it is displayed that the elapsed time/accuracy management interval is 10/100 for AST, ALT, and ALP. It is also necessary to perform accuracy management of the analysis item LDH by the analytical unit 3E using a control sample of a lot number of S668795 with a name of Ctrl-2 and a type of Ser/P1, and it is displayed that the elapsed time/accuracy management interval is 50/60. Furthermore, it is necessary to perform accuracy management of the analysis item TP by the analytical unit 3E using a control sample of a lot number of S668795 with a name of Ctrl-2 and a type of Ser/P1, and it is displayed that the elapsed time/accuracy management interval is 50/60. Furthermore, it is necessary to perform accuracy management of the analysis item UN by the analytical unit 3F using a control sample of a lot number of V846852 with a name of Ctrl-U and a type of Urin, and it is displayed that the elapsed time/accuracy management interval is 10/60. Furthermore, it is necessary to perform accuracy management of the analysis item CRE by the analytical unit 3F using a control sample of a lot number of S668795 with a name of Ctrl-2 and a type of Ser/P1, and it is displayed that elapsed time the/accuracy management interval is 50/60. Furthermore, it is necessary to perform accuracy management of the analysis item CRP by the analytical unit 3D using a control sample of a lot number of M970123 with a name of Ctrl-M and a type of Ser/P1, and it is displayed that the elapsed time/accuracy management interval is 10/60.

It is also possible that one of the buttons 505 to 507 is instructed, a list of analysis items is displayed in the display area 510, and the information on a control sample necessary for accuracy management of each analysis item is associated with each analysis item and outputted from the printer 44 at the same time.

When there are many analysis items displayed in the display area 510 and all of them cannot be displayed at one time, it is possible to display the analysis items by scrolling the display area 510 by the button 551 or 552.

Next, the buttons other than the above which are displayed on the accuracy management support screen will be explained. When the Select button 531 is instructed by an operator, the list displayed on the screen can be edited. When the Save button 532 is instructed by an operator, the list displayed on the screen will be saved. When the Help button 533 is instructed by an operator, the help information will be displayed.

Next, the operation of this support system will be explained. The program specifying the operation of this support system is stored in the storage part 45 and when the total control computer 40 reads and executes this program, the operation of this support system will be performed.

Figure 6:
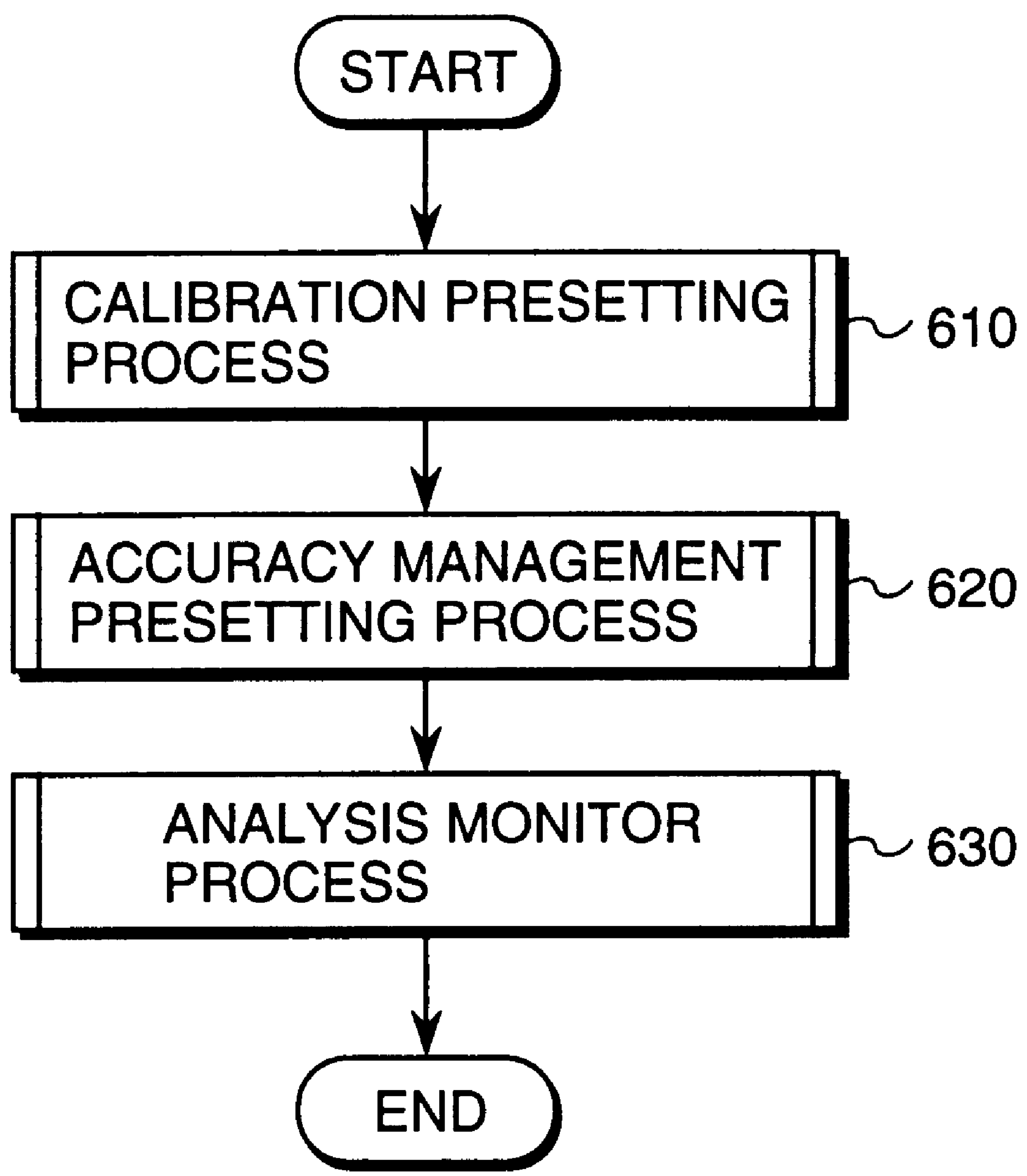
FIG. 6 is a flow chart showing the outline of operation of the support system of the present invention.

FIG. 6 is a flow chart showing the outline of the operation of this support system. Firstly, at Step 610, the supporting system calls the calibration presetting process routine. Next, at Step 620, the supporting system calls the accuracy management presetting process routine. Thereafter, at Step 630, the supporting system calls, executes, and finishes the analysis monitor process routine.

Figure 7:
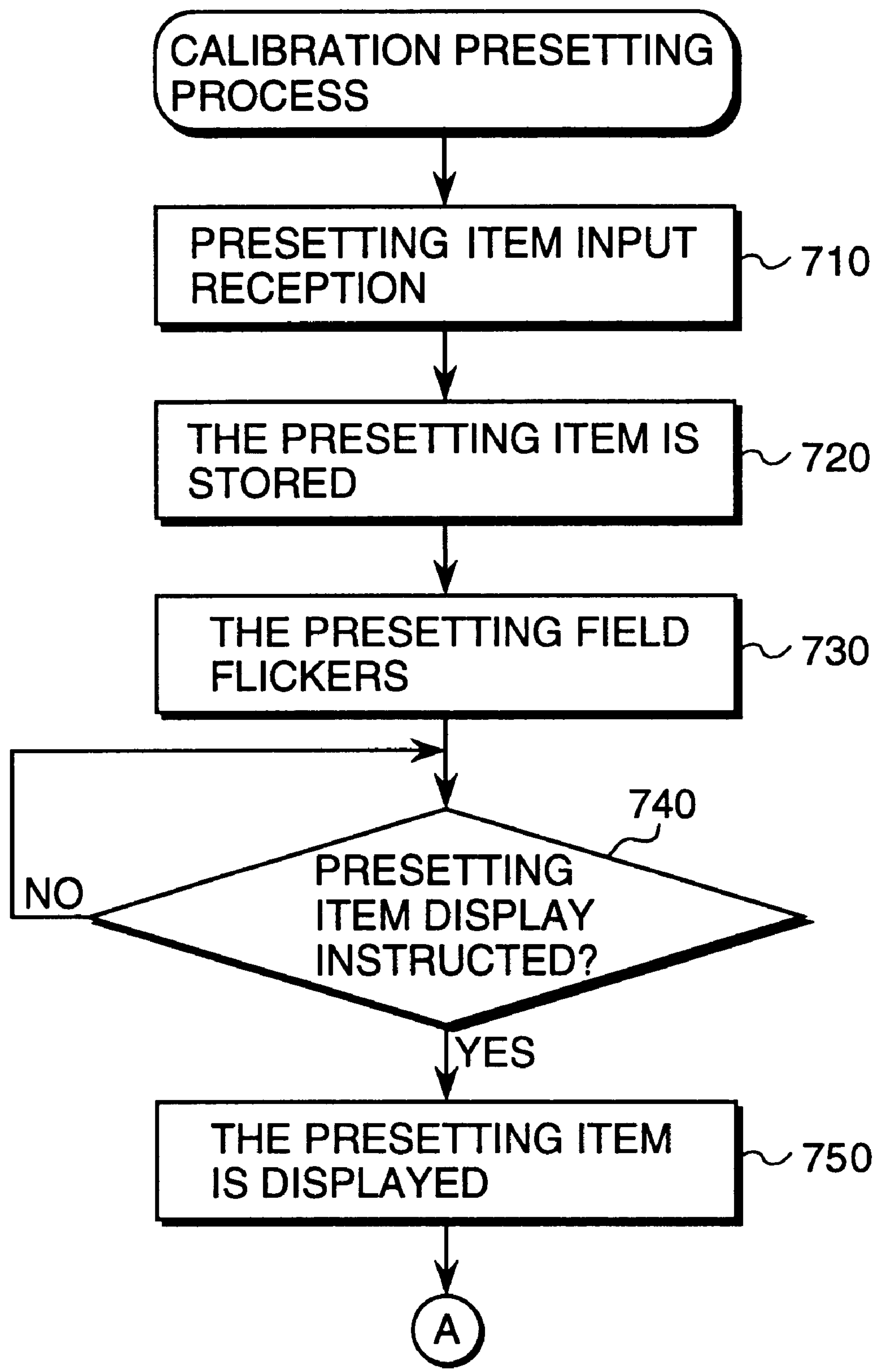
FIG. 7 is a flow chart showing the calibration presetting process of the support system of the present invention.

FIGS. 7 and 8 show detailed flow charts of the calibration presetting process routine to be started at Step 610. Firstly, at Step 710, the calibration presetting process routine receives input of the calibration presetting item which is an analysis item for which calibration is to be stationarily performed. The calibration presetting item is inputted from the operator console 42 by an operator.

The calibration presetting item may be inputted once and then updated unless it is changed every day. Or, when some item is changed, such as increased or decreased, it is possible to input only the item and update the others.

Next, at Step 720, the calibration presetting process routine stores the inputted calibration presetting item in the storage part 45. When the calibration presetting item is stored in the storage part 45, at Step 730, the routine allows the Presetting display block 401 on the calibration support screen shown in FIG. 4 to flicker. Next, at Step 740, the routine decides whether the button 405 is instructed (display instruction of the calibration presetting item) by an operator. When it is decided at Step 740 that the button 405 is not instructed by an operator, the routine waits for input of a display instruction. When it is decided at Step 740 that the button 405 is instructed by an operator, the routine goes to Step 750 and displays the calibration presetting item in the display area 410 on the calibration support screen shown in FIG. 4.

Next, at Step 810, the routine instructs execution of one calibration among the calibration presetting items. Then, at Step 820, the routine decides whether the calibration (the calibration whose execution is instructed at Step 810) succeeds or not. When it is decided at Step 820 that the calibration fails, the routine goes to Step 870, calls and executes the calibration failure recovery process routine, and returns to Step 820. When it is decided at Step 820 that the calibration succeeds, the routine goes to Step 830 and resets the calibration time stored in the storage part 45 for the analysis item of this calibration.

Next, at Step 840, the routine erases the display of the analysis item of the calibration among the calibration presetting items displayed in the display area 410 on the calibration support screen shown in FIG. 4. Next, at Step 850, the routine erases the storage of the analysis item of the calibration among the presetting items stored in the storage part 45.

Next, at Step 860, the routine decides whether the calibration of all analysis items among the calibration presetting items ends or not. When it is decided at Step 860 that there are analysis items among the presetting items which have not finished calibration yet, the routine returns to Step 860. When it is decided at Step 860 that the calibration of all analysis items among the presetting items ends, the routine returns.

Next, FIG. 9 shows a detailed flow chart of the calibration failure recovery process routine to be started at Step 870 in the aforementioned calibration presetting process routine. Firstly, at Step 910, the calibration failure recovery process routine stores the analysis item whose calibration fails in the storage part 45 as a calibration failed item. Next, at Step 920, the routine allows the Calib. Failed display block 403 on the calibration support screen shown in FIG. 4 to flicker. Next, at Step 930, the routine decides whether the button 407 is instructed (display instruction of the Calib. Failed item) by an operator. When it is decided at Step 930 that the button 407 is not instructed by an operator, the routine waits for input of a display instruction. When it is decided at Step 930 that the button 407 is instructed by an operator, the routine goes to Step 940 and displays the Calib. Failed item in the display area 410 on the calibration support screen shown in FIG. 4. Next, at Step 950, the routine instructs execution of calibration of the Calib. Failed item. Thereafter, the routine goes to Step 960 and erases the analysis item of the calibration among the display of the Calib. Failed items displayed in the display area 410 on the calibration support screen shown in FIG. 4. Next, at Step 970, the routine erases the storage of the analysis item of the calibration among the Calib. Failed items stored in the storage part 45 and returns.

Figure 10:
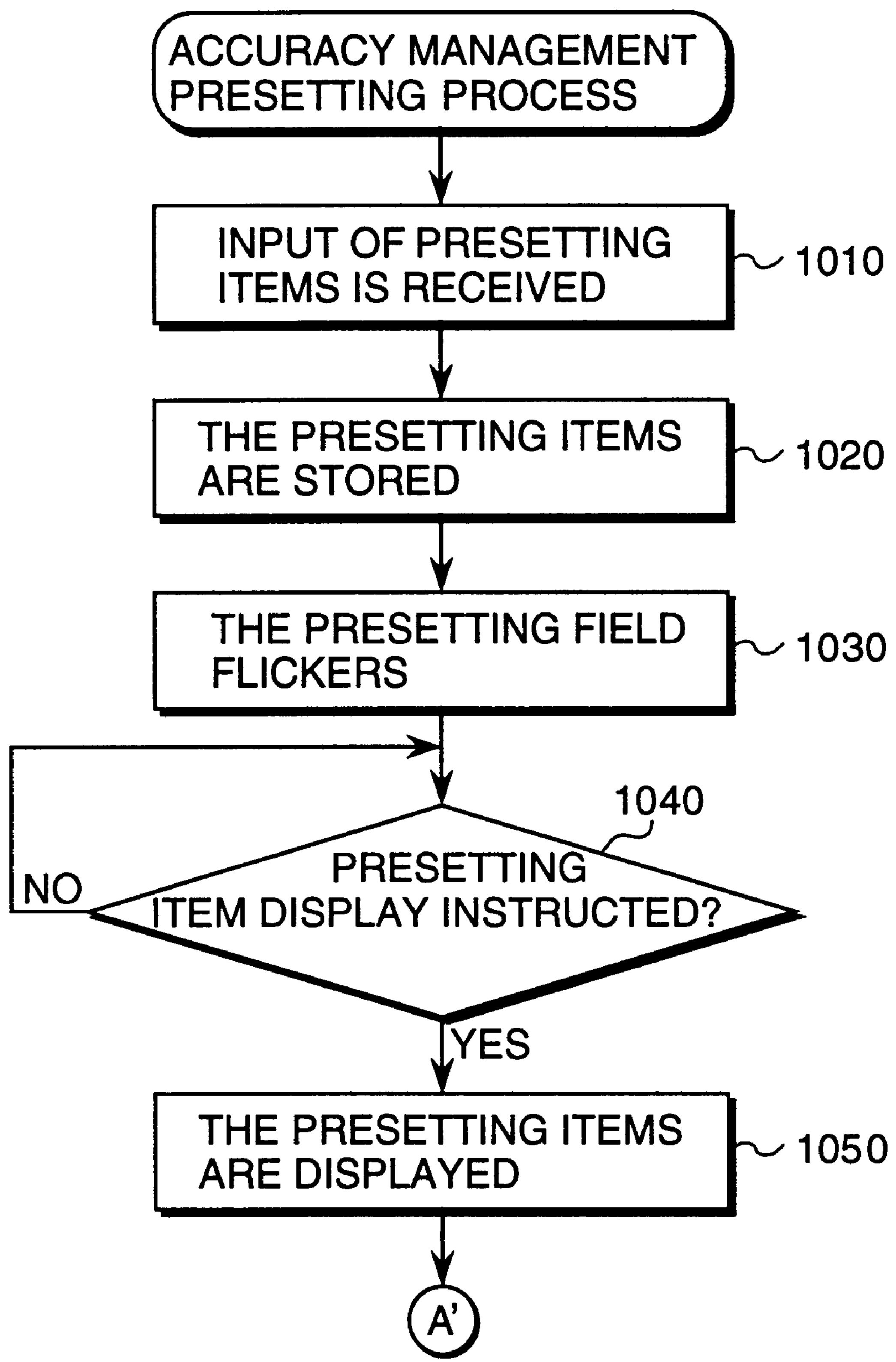
FIG. 10 is a flow chart showing the accuracy management presetting process of the support system of the present invention.

FIGS. 10 and 11 are detailed flow charts of the accuracy management presetting process routine to be started at Step 620 in the flow chart showing the outline of the operation of this support system shown in FIG. 6. Firstly, at Step 1010, the accuracy management presetting process routine receives input of the accuracy management presetting item which is an analysis item for which accuracy management is to be stationarily performed. The accuracy management presetting item is inputted from the operator console 42 by an operator.

Next, at Step 1020, the accuracy management presetting process routine stores the inputted accuracy management presetting items in the storage part 45. When the accuracy management presetting items are stored in the storage part 45, at Step 1030, the routine allows the Pre-setting display block 501 on the accuracy management support screen shown in FIG. 5 to flicker. Next, at Step 1040, the routine decides whether the button 505 is instructed (display instruction of the accuracy management presetting items) by an operator. When it is decided at Step 1040 that the button 505 is not instructed by an operator, the routine waits for input of a display instruction. When it is decided at Step 1040 that the button 505 is instructed by an operator, the routine goes to Step 1050 and displays the accuracy management presetting items in the display area 510 on the accuracy management support screen shown in FIG. 5.

Next, at Step 1110, the routine instructs execution of one accuracy management among the accuracy management presetting items. Then, at Step 1120, the routine decides whether the accuracy management (the accuracy management whose execution is instructed at Step 1110) succeeds or not. When it is decided at Step 1120 that the accuracy management fails, the routine goes to Step 1170, calls and executes the accuracy management recovery process routine, and returns to Step 1120. When it is decided at Step 1120 that the accuracy management succeeds, the routine goes to Step 1130 and resets the accuracy management time stored in the storage part 45 for the analysis item of this accuracy management. Next, at Step 1140, the routine erases the display of the analysis item of the accuracy management among the accuracy management presetting items displayed in the display area 510 on the accuracy management support screen shown in FIG. 5. Next, at Step 1150, the routine erases the storage of the analysis item of the accuracy management among the accuracy management presetting items stored in the storage part 45.

Next, at Step 1160, the routine decides whether the accuracy management of all analysis items among the accuracy management presetting items ends or not. When it is decided at Step 1160 that there are analysis items among the accuracy management presetting items which have not finished accuracy management yet, the routine returns to Step 1110. When it is decided at Step 1160 that the accuracy management of all analysis items among the accuracy management presetting items ends, the routine returns.

Figure 12:
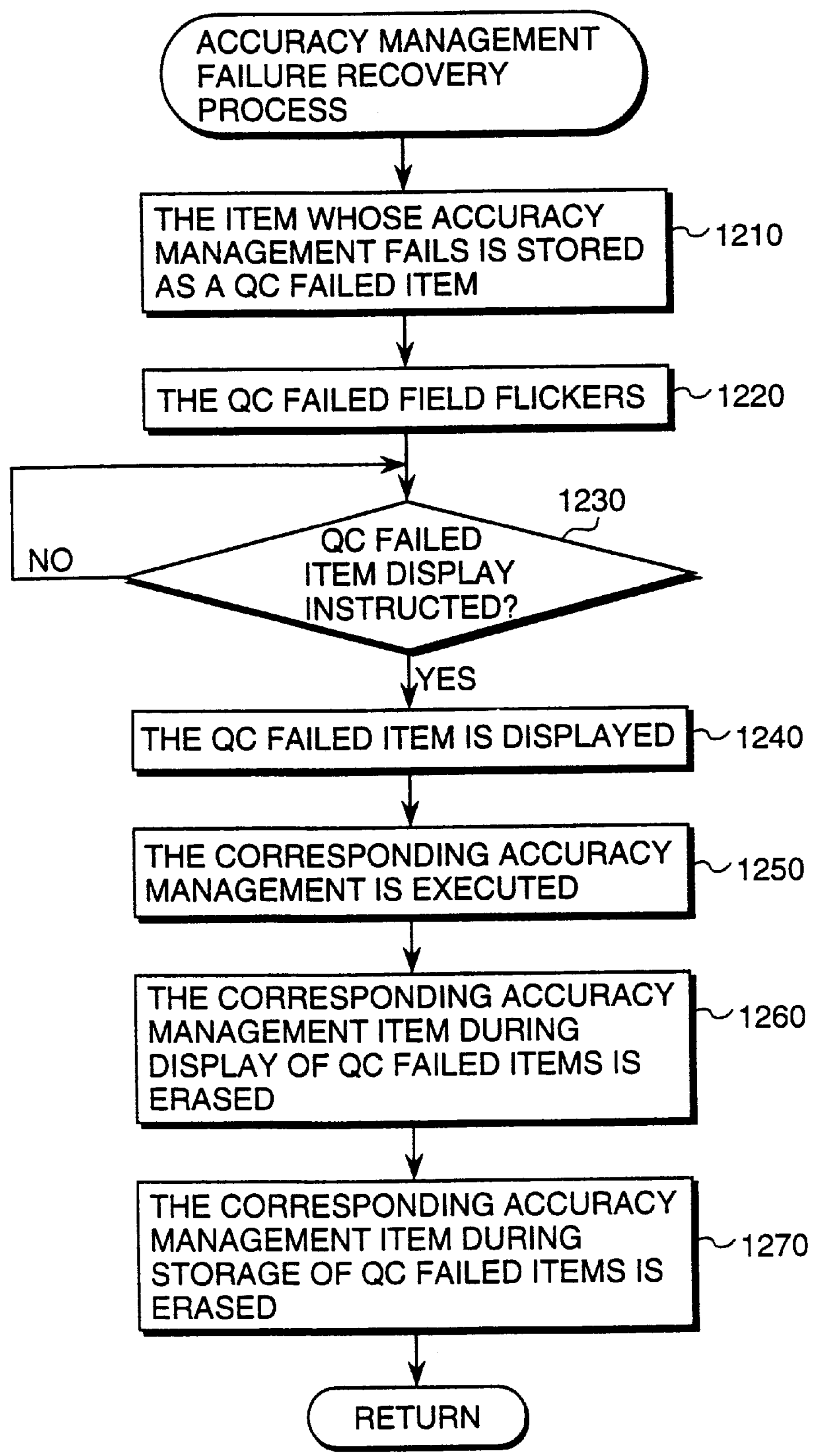
FIG. 12 is a flow chart showing the accuracy management failure recovery process of the support system of the present invention.

Next, FIG. 12 shows a detailed flow chart of the accuracy management failure recovery process routine to be started at Step 1170 in the aforementioned accuracy management presetting process routine. Firstly, at Step 1210, the accuracy management failure recovery process routine stores the analysis item whose accuracy management fails in the storage part 45 as a QC failed item. Then, at Step 1220, the routine allows the QC Failed field 503 (FIG. 5) to flicker. Next, at Step 1230, the routine decides whether the button 507 is instructed (display instruction of the QC Failed item) by an operator.

When it is decided at Step 1230 that the button 507 is not instructed by an operator, the routine waits for input of a display instruction. When it is decided at Step 1230 that the button 507 is instructed by an operator, the routine goes to Step 1240 and displays the QC Failed item in the display area 510 on the accuracy management support screen shown in FIG. 5.

Next, at Step 1250, the routine instructs execution of accuracy management of the QC Failed item. Thereafter, the routine goes to Step 1260 and erases the analysis item of the accuracy management among the display of the QC Failed item displayed in the display area 510 on the accuracy management support screen shown in FIG. 5. Next, at Step 1270, the routine erases the storage of the analysis item of the accuracy management among the QC Failed item stored in the storage part 45 and returns.

Figure 13:
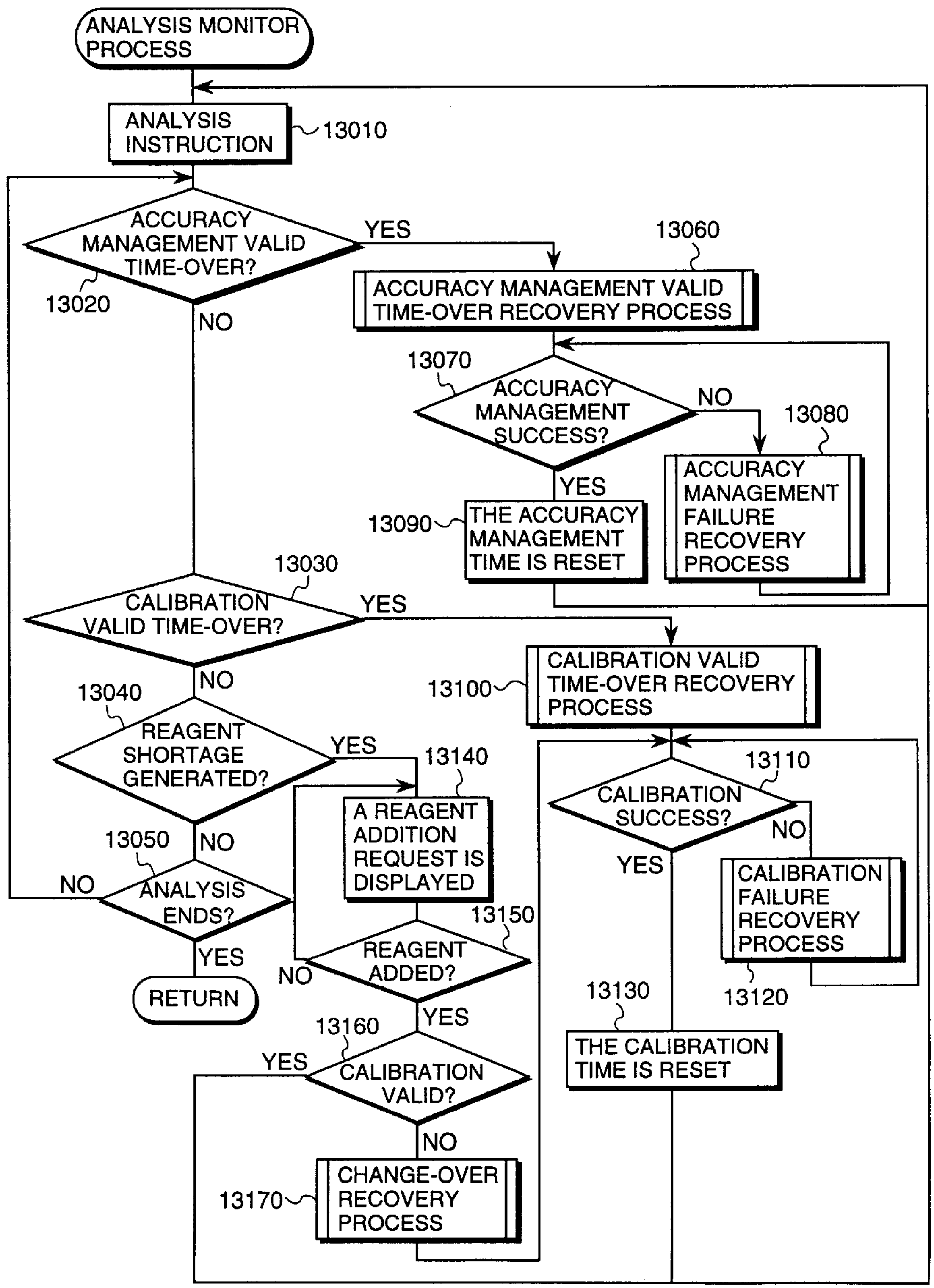
FIG. 13 is a flow chart showing the analysis monitor process of the support system of the present invention.

FIG. 13 is a detailed flow chart of the analysis monitor process routine to be started at Step 630 in the flow chart showing the outline of the operation of this support system shown in FIG. 6. Firstly, at Step 13010, the analysis monitor process routine instructs each analytical unit of the automatic analyzers to execute analysis. Next, at Step 13020, the routine decides whether there is an analysis item for which the reliable time of accuracy management has elapsed or not. When it is decided at Step 13020 that there is an analysis item for which the, reliable time of accuracy management has elapsed, the routine goes to Step 13060 and calls and executes the accuracy management reliable time-over recovery process routine.

Next, at Step 13070, the routine decides whether the accuracy management executed in the accuracy management reliable time-over recovery process routine succeeds or not. When it is decided at Step 13070 that the accuracy management executed in the accuracy management reliable time-over recovery process routine succeeds, the routine goes to Step 13090 and resets the accuracy management time of the analysis item of this accuracy management stored in the storage part 45. Thereafter, the routine returns to Step 13010. When it is decided at Step 13070 that the accuracy management executed in the accuracy management reliable time-over recovery process routine fails, the routine goes to Step 13080, calls and executes the aforementioned accuracy management failure recovery process routine, and then returns to Step 13070. When it is decided at Step 13020 that there is no analysis item for which the reliable time of accuracy management has elapsed, the routine goes to Step 13030.

At Step 13030, the routine decides whether there is an analysis item for which the reliable time of calibration has elapsed or not. When it is decided at Step 13030 that there is an analysis item for which the reliable time of calibration has elapsed, the routine goes to Step 13100 and calls the calibration reliable time-over recovery process routine and executes the calibration of the analysis item.

Next, at Step 13110, the routine decides whether the calibration executed in the calibration reliable time-over recovery process routine succeeds or not. When it is decided at Step 13110 that the calibration executed in the calibration reliable time-over recovery process routine succeeds, the routine goes to Step 13130 and resets the calibration time of the analysis item of this calibration stored in the storage part 45. Thereafter, the routine returns to Step 13010. When it is decided at Step 13110 that the calibration executed in the calibration reliable time-over recovery process routine fails, the routine goes to Step 13120, calls and executes the aforementioned calibration failure recovery process routine, and then returns to Step 13110. When it is decided at Step 13030 that there is no analysis item for which the reliable time of calibration has elapsed, the routine goes to Step 13040 and decides whether reagent shortage occurs and it is necessary to add a reagent bottle or not.

When it is decided at Step 13040 that it is not necessary to add a reagent bottle, the routine goes to Step 13050 and decides whether all analyses have ended or not. When it is decided at Step 13050 that there is still an analysis to be executed, the routine returns to Step 13020. When it is decided at Step 13050 that all analyses have ended, the routine returns. When it is decided at Step 13040 that it is necessary to add a reagent bottle, the routine goes to Step 13040 and displays the necessity of addition of a reagent bottle on the display screen of the CRT 43.

Next, at Step 13150, the routine decides whether a reagent bottle has been added or not. When it is decided at Step 13150 that no reagent bottle is added, the routine returns to Step 13140. When it is decided at Step 13150 that a reagent bottle has been added, the routine goes to Step 13160 and decides whether it is necessary to execute the calibration accompanying addition of the reagent bottle or not on the basis of the information stored in the storage part 45. When it is decided at Step 13160 that it is not necessary to execute the calibration accompanying addition of the reagent bottle, the routine returns to Step 13010. When it is decided at Step 13160 that it is necessary to execute the calibration accompanying addition of the reagent bottle, the routine goes to Step 13170, calls and executes the change over recovery processing routine, and then goes to Step 13110.

Figure 14:
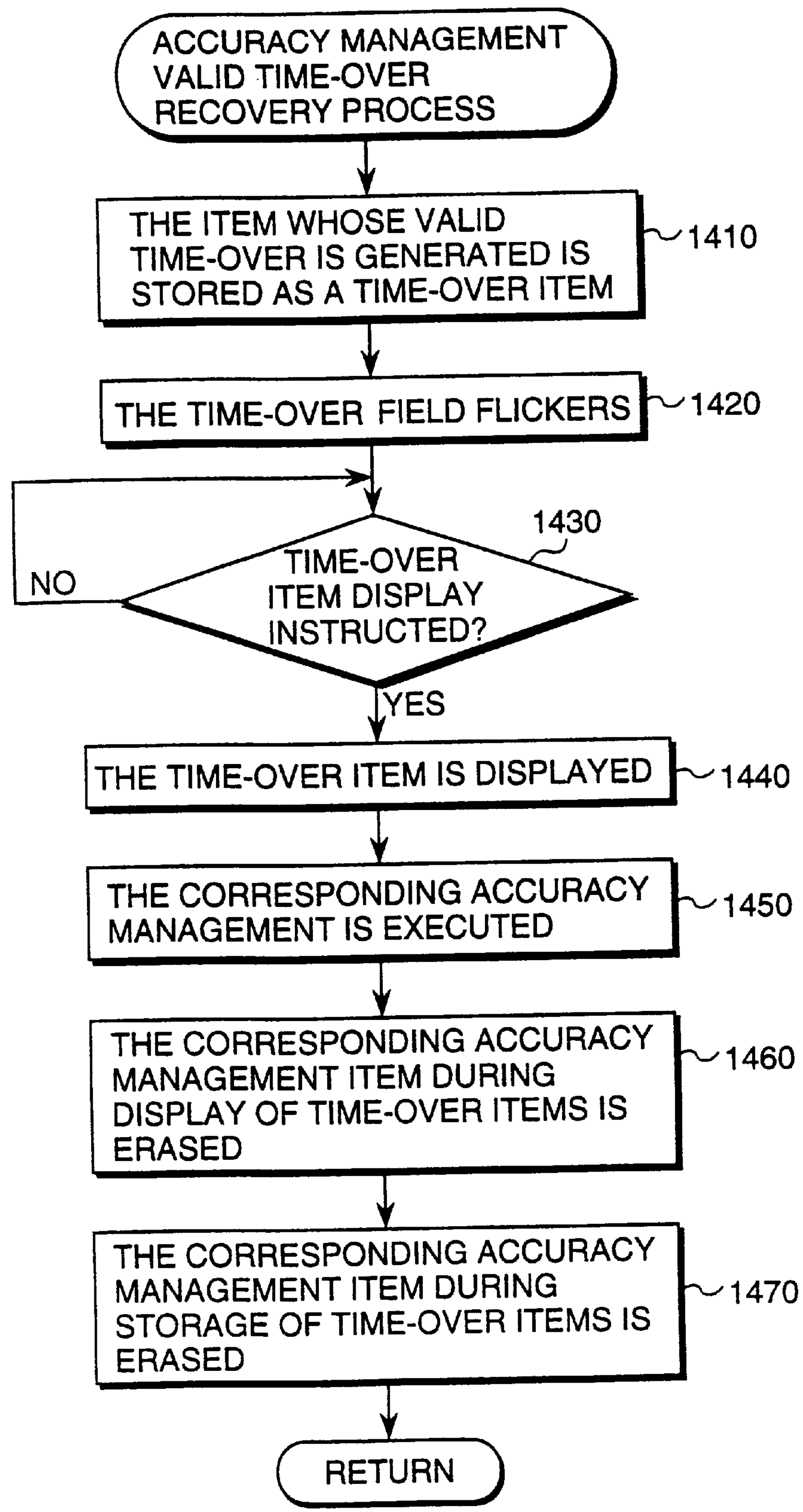
FIG. 14 is a flow chart showing the accuracy management reliable time-over recovery process of the support system of the present invention.

Next, FIG. 14 is a detailed flow chart of the accuracy management reliable time-over recovery process routine to be called at Step 13060 in the aforementioned analysis monitor process routine. Firstly, at Step 1410, the accuracy management reliable time-over recovery process routine stores an analysis item for which the reliable time of accuracy management elapses in the storage part 45 as a time-over item. Next, at Step 1420, the routine allows the Time-over display block 502 on the accuracy management support screen shown in FIG. 5 to flicker. Next, at Step 1430, the routine decides whether the button 506 is instructed (display instruction of the time-over item) by an operator. When it is decided at Step 1430 that the button 506 is not instructed by an operator, the routine waits for input of a display instruction. When it is decided at Step 1430 that the button 506 is instructed by an operator, the routine goes to Step 1440 and displays the time-over item in the display area 510 on the accuracy management support screen shown in FIG. 5. Next, at Step 1450, the routine instructs execution of accuracy management of the time-over item. Thereafter, the routine goes to Step 1460 and erases the analysis item of the accuracy management among the display of the time-over items displayed in the display area 510 on the accuracy management support screen shown in FIG. 5. Next, at Step 1470, the routine erases the storage of the analysis item of, the accuracy management among the time-over items stored in the storage part 45 and returns.

Next, FIG. 15 is a detailed flow chart of the calibration reliable time-over recovery process routine to be started at Step 13100 in the aforementioned analysis monitor process routine. Firstly, at Step 1510, the calibration reliable time-over recovery process routine stores an analysis item for which the reliable time of calibration has elapsed in the storage part 45 as a Calib. Now item. Next, at Step 1520, the routine allows the Calib. Now display block 402 on the calibration support screen shown in FIG. 4 to flicker. Next, at Step 1530, the routine decides whether the button 406 is instructed (display instruction of the Calib. Now item) by an operator. When it is decided at Step 1530 that the button 406 is not instructed by an operator, the routine waits for input of a display instruction.

When it is decided at Step 1530 that the button 406 is instructed by an operator, the routine goes to Step 1540 and displays the Calib. Now item in the display area 410 on the calibration support screen shown in FIG. 4. Next, at Step 1550, the routine instructs execution of calibration of the Calib. Now item. Thereafter, the routine goes to Step 1560 and erases the analysis item of the calibration among the display of the Calib. Now items displayed in the display area 410 on the calibration support screen shown in FIG. 4. Next, at Step 1570, the routine erases the storage of the analysis item of the calibration among the Calib. Now items stored in the storage part 45 and returns.

Figure 16:
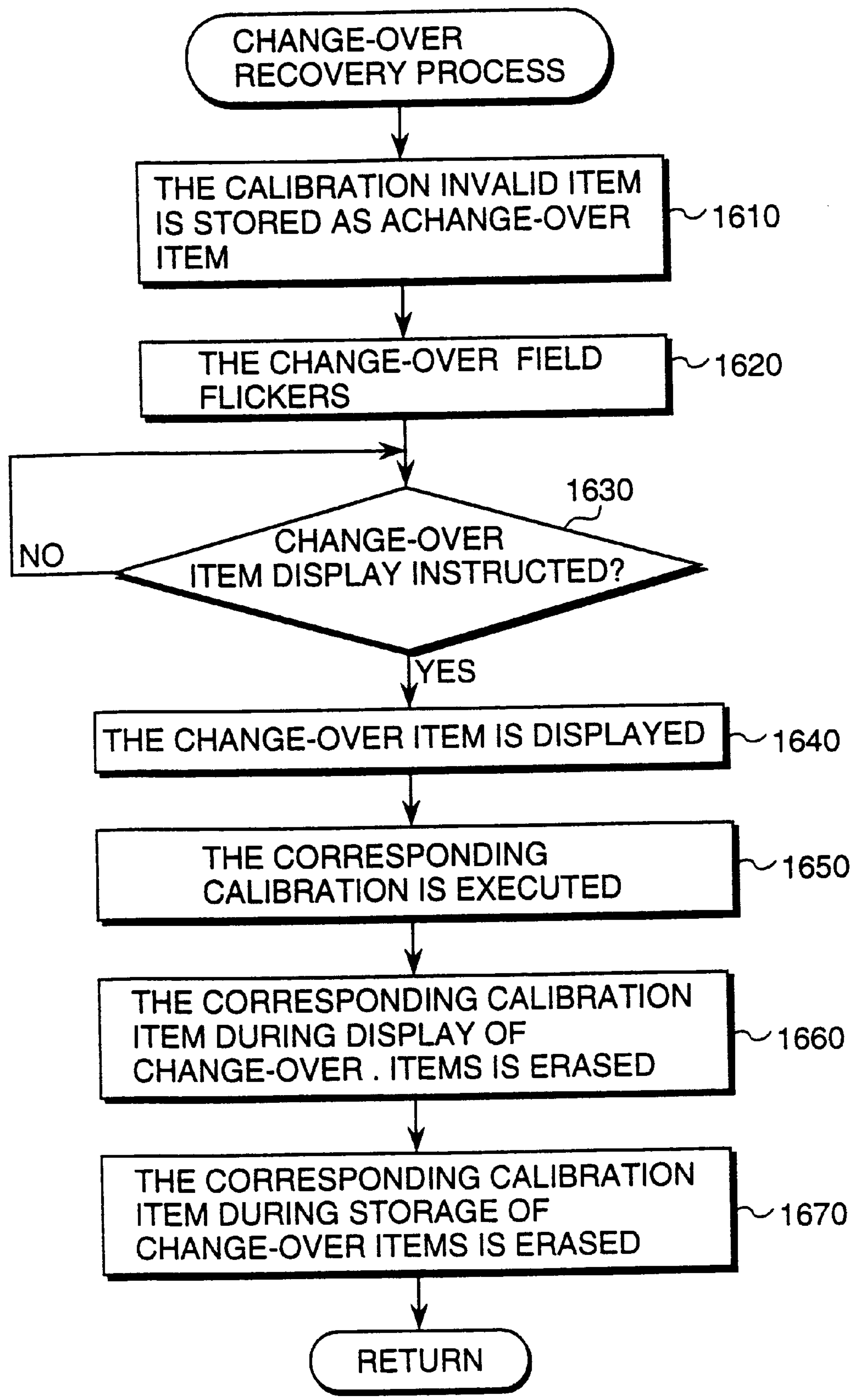
FIG. 16 is a flow chart showing the change over recovery process of the support system of the present invention.

Next, FIG. 16 is a detailed flow chart of the change over recovery process routine to be started at Step 13170 in the aforementioned analysis monitor process routine. Firstly, at Step 1610, the change over recovery process routine stores an analysis item for which calibration is required to be performed in correspondence with an addition or update of a reagent bottle in the storage part 45 as a change over item. Next, at Step 1620, the routine allows the Change Over display block 404 on the calibration support screen shown in FIG. 4 to flicker. Next, at Step 1630, the routine decides whether the button 408 is instructed (display instruction of the Change Over item) by an operator. When it is decided at Step 1630 that the button 408 is not instructed by an operator, the routine waits for input of a display instruction. When it is decided at Step 1630 that the button 408 is instructed by an operator, the routine goes to Step 1640 and displays the Change Over item in the display area 410 on the calibration support screen shown in FIG. 4. Next, at Step 1650, the routine instructs execution of calibration of the Change Over item. Thereafter, the routine goes to Step 1660 and erases the analysis item of the calibration among the display of the Change Over items displayed in the display area 410 on the calibration support screen shown in FIG. 4. Next, at Step 1670, the routine erases the storage of the analysis item of the calibration among the Change Over items stored in the storage part 45 and returns.

FIG. 17 is a flow chart showing a detailed execution process of calibration at Step 810 shown in FIG. 8, Step 950 shown in FIG. 9, Step 1550 shown in FIG. 15, and Step 1650 shown in FIG. 16.

Firstly, at Step 1710, the calibration execution process instructs start of the automatic analyzer. Next, at Step 1720, the calibration execution process specifies the reference sample rack 74 necessary for calibration of the analysis item to be executed from the data in which each analysis item and the information on a reference sample necessary for calibration of each analysis item are stored in correspondence with each other. The calibration execution process obtains the address of the reference sample rack 74 on the rotor 76 necessary for calibration of the analysis item to be executed from the data stored in the storage part 45 in which each reference sample rack and the position (address) of the reference sample rack on the rotor 76 are stored in correspondence with each other.

Next, at Step 1730, the calibration execution process rotates the rotor 76 by the drive means 73 by detecting the position with the sensor 72 and stops the reference sample rack 74 at the aforementioned address in front of the inlet to the main transfer line 20. Next, at Step 1740, the calibration execution process instructs to put the reference sample rack 74 onto the main transfer line 20. Next, at Step 1750, the calibration execution process decides which analytical unit is to be selected so as to execute the analysis item calibration to be executed.

Next, at Step 1760, the calibration execution process controls the main transfer line 20 so as to transfer the reference sample rack 74 to the analytical unit which is decided to perform calibration. When the aforementioned reference sample rack 74 is transferred to the analytical unit which is decided to perform calibration, at Step 1770, the calibration execution process instructs the corresponding analytical unit to execute calibration by use of the reference sample on the reference sample rack 74. Upon receipt of this instruction, the aforementioned analytical unit executes the calibration of the analysis item to be executed.

FIG. 18 is a flow chart showing a detailed execution process of accuracy management at Step 1110 shown in FIG. 11, Step 1250 shown in FIG. 12, and Step 1450 shown in FIG. 14. Firstly, at Step 1810, the accuracy management execution process instructs start of the automatic analyzer. Next, at Step 1820, the accuracy management execution process specifies the control sample rack 77 necessary for accuracy management of the analysis item to be executed from the data in which each analysis item and the information on a control sample necessary for accuracy management of each analysis item are stored in correspondence with each other. The accuracy management execution process obtains the address of the control sample rack 77 on the rotor 76 necessary for accuracy management of the analysis item to be executed from the data stored in the storage part 45 in which each control sample rack and the position (address) of the control sample rack on the rotor 76 are stored in correspondence with each other.

Next, at Step 1830, the accuracy management execution process rotates the rotor 76 by the drive means 73 by detecting the position with the sensor 72 and stops the control sample rack 77 at the aforementioned address in front of the inlet to the main transfer line 20. Next, at Step 1840, the accuracy management execution process instructs to put the control sample rack 77 onto the main transfer line 20. Next, at Step 1850, the accuracy management execution process decides which analytical unit is to be selected so as to execute the analysis item accuracy management to be executed. Next, at Step 1860, the accuracy management execution process controls the Amain transfer line 20 so as to transfer the aforementioned control sample rack 77 to the analytical unit which is decided to perform accuracy management. When the aforementioned control sample rack 77 is transferred to the analytical unit which is decided to perform accuracy management, at Step 1870, the accuracy management execution process instructs the aforementioned analytical unit to execute accuracy management by use of the control sample on the control sample rack 77. Upon receipt of this instruction, the aforementioned analytical unit executes the analysis item accuracy management to be executed.

The display blocks 401 to 404 shown in FIG. 4 and the display blocks 501 to 503 shown in FIG. 5 are classification captions corresponding to the necessity state of calibration or accuracy management. The display blocks positioned on the upper part of the screen among the display blocks 401 to 404 shown in FIG. 4 and the display blocks 501 to 503 shown in FIG. 5 are set so that their priorities are above those of the display blocks positioned on the lower part.

When a classification state requiring two or more calibrations or accuracy managements regarding the same analysis item occurs, the corresponding two or more display blocks flicker. When execution of calibration or accuracy management is instructed from the receiving button corresponding to one higher-priority display block among the flickering display blocks, the automatic analyzer executes the instruction. By doing this, the necessity of calibration or accuracy management corresponding to the lower-priority display blocks is canceled, so that the flickering status of the residual display blocks which are not instructed is eliminated and the storage information relating to occurrence of necessity is erased.

In the explanation of the operation of the support system, when the analysis items to be set as a presetting item, Calib. Now item, Calib. Failed item, Change Over item, Time Over item, and QC Failed item are stored in the storage part 45 respectively and the stored analysis items are hit, it is possible to set them as a presetting item, Calib. Now item, Calib. Failed item, Change Over item, Time Over item, and QC Failed item.

Next, to realize the operation of the aforementioned support system, the structure of data stored in the storage part 45 will be explained. FIG. 19 shows the structure of data. In the storage part 45, as shown in FIG. 19, calibration information 1900 and accuracy management information 1910 are stored. The calibration information 1900 stores the calibration time interval, elapsed time of the corresponding analysis item executed previously from calibration (or the calibration time of the corresponding analysis item previously executed), calibration execution format (the reference sample name used for calibration, calibration method, etc.), calibration parameter (information on the formula of calibration curve), calibration execution condition (information on which case is to be selected for execution of calibration), and others for each analysis item. The accuracy management information 1910 stores the accuracy management time interval, elapsed time of the corresponding analysis item executed previously from accuracy management (or the accuracy management time of the corresponding analysis item previously executed), accuracy management execution format (the control sample name used for accuracy management, accuracy management method, etc.), accuracy management execution condition (information on which case is to be selected for execution of accuracy management), and others for each analysis item. The whole control computer 40 performs calibration and accuracy management by referring to the calibration information 1900 and the accuracy management information 1910 when necessary.

Figure 20:
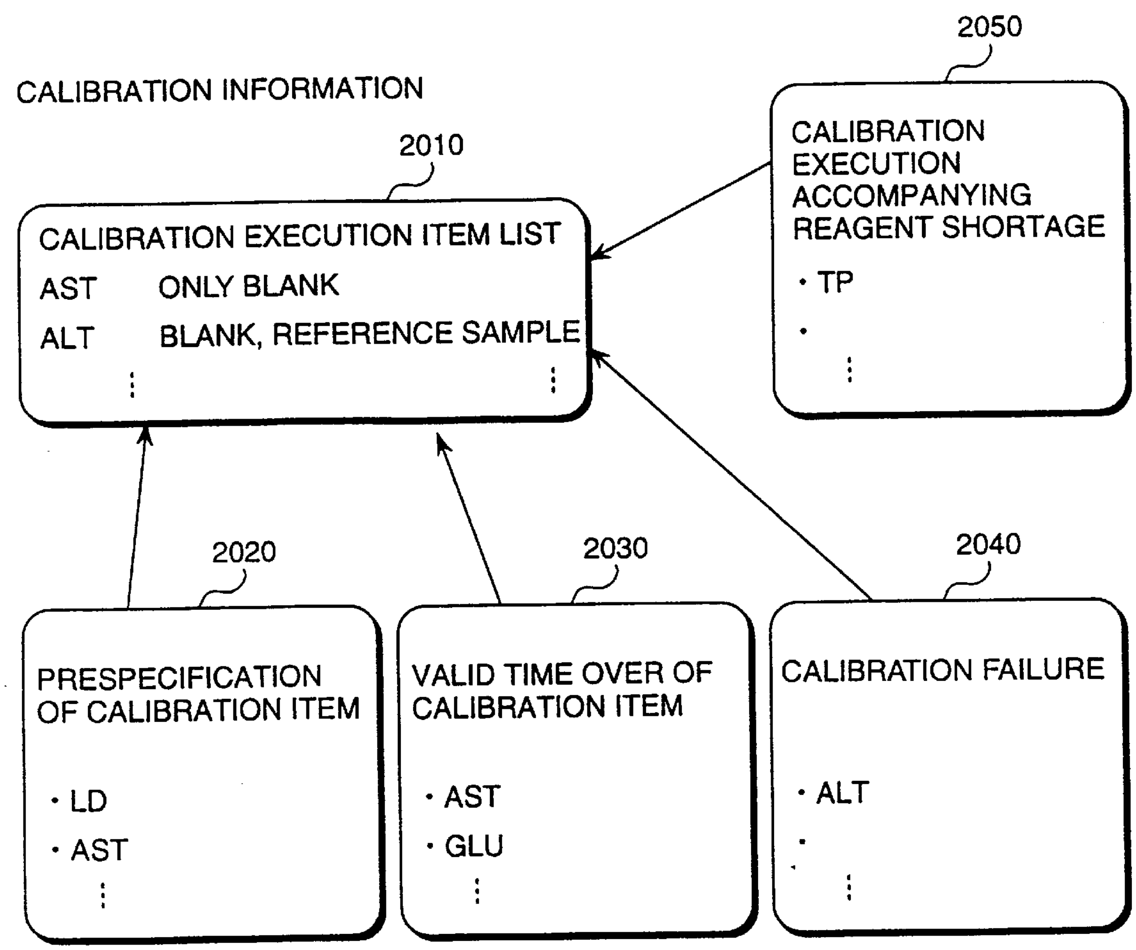
FIG. 20 is a drawing for explaining the mutual relationship of data to be stored by the support system of the present invention.

FIG. 20 shows the mutual relationship of data on calibration which occurs in correspondence with the operation of the aforementioned support system and is stored in the storage part 45.

Firstly, a first example of the aforementioned mutual relationship of data will be shown.

As preset data 2020 of a calibration item, an analysis item whose calibration is stationarily executed is preset by an operator. As reliable time-over data 2030 of a calibration item, an analysis item whose calibration is re-executed is preset by an operator when the calibration time interval elapses. As calibration failure data 2040, an analysis item whose calibration is re-executed is preset by an operator when the calibration fails. As calibration execution data 2050 accompanying reagent shortage, an analysis item whose calibration is re-executed is preset by an operator when a reagent bottle is added.

When the automatic analyzer is in the state of executing the calibration to be executed stationarily, this support system reads the preset data 2020 of a calibration item, generates a calibration execution item list 2010 storing the analysis item for which calibration is to be executed and the reference sample in correspondence with each other by referring to the calibration information 1900 (see FIG. 19) regarding the analysis item which is set as preset data 2020 of a calibration item, and executes calibration on the basis of the calibration execution item list 2010.

When a calibration whose time interval as a reliable time has elapsed, this support system decides whether the analysis item of this calibration is set as reliable time-over data 2030 of a calibration item or not. When it is decided that the analysis item of this calibration is set as reliable time-over data 2030 of a calibration item, the support system generates a calibration execution item list 2010 storing the analysis item for which calibration is to be executed and the reference sample in correspondence with each other by referring to the calibration information 1900 (see FIG. 19) regarding the analysis item, and executes calibration on the basis of the calibration execution item list 2010. When it is decided that the analysis item of this calibration is not set as reliable time-over data 2030 of a calibration item, the support system will not generate a calibration execution item list 2010.

When the calibration fails, this support system decides whether the analysis item of this calibration is set as calibration failure data 2040 or not. When it is decided that the analysis item of this calibration is set as calibration failure data 2040, the support system generates a calibration execution item list 2010 storing the analysis item for which calibration is to be executed and the reference sample in correspondence with each other by referring to the calibration information 1900 (see FIG. 19) regarding the analysis item and executes calibration on the basis of the calibration execution item list 2010. When it is decided that the analysis item of this calibration is not set as calibration failure data 2040, the support system will not generate a calibration execution item list 2010.

When a reagent bottle is added or exchanged, this support system decides whether the analysis item of this calibration is set as calibration execution data 2050 accompanying reagent shortage or not. When it is decided that the analysis item of this calibration is set as calibration execution data 2050 accompanying reagent shortage, the support system generates a calibration execution item list 2010 storing the analysis item for which calibration is to be executed and the reference sample in correspondence with each other by referring to the calibration information 1900 (see FIG. 19) regarding the analysis item, and executes calibration on the basis of the calibration execution item list 2010. When it is decided that the analysis item of this calibration is not set as calibration execution data 2050 accompanying reagent shortage, the support system will not generate a calibration execution item list 2010.

Next, a second example of the mutual relationship of data on calibration will be shown.

As preset data 2020 of a calibration item, the Pre-Setting item received at Step 710 of the calibration presetting process shown in FIG. 7 is stored. The reliable time-over data 2030 of a calibration item is the Calib. Now item stored at Step 1510 of the calibration reliable time-over recovery process shown in FIG. 15. The calibration failure data 2040 is the Calib. Failed item stored at Step 910 of the calibration failure recovery process shown in FIG. 9. The calibration execution data 2050 accompanying cai reagent shortage is the Change Over item stored at Step 1610 of the change over recovery process shown in FIG. 9. When these preset data 2020 of a calibration item, reliable time-over data 2030 of a calibration item, calibration failure data 2040, and calibration execution data 2050 accompanying reagent shortage occur, the whole control computer 40 generates a calibration execution item list 2010 storing the analysis item for which calibration is to be executed and the reference sample in correspondence with each other by referring to the calibration information 1900, and executes calibration on the basis of the calibration execution item list 2010.

Figure 21:
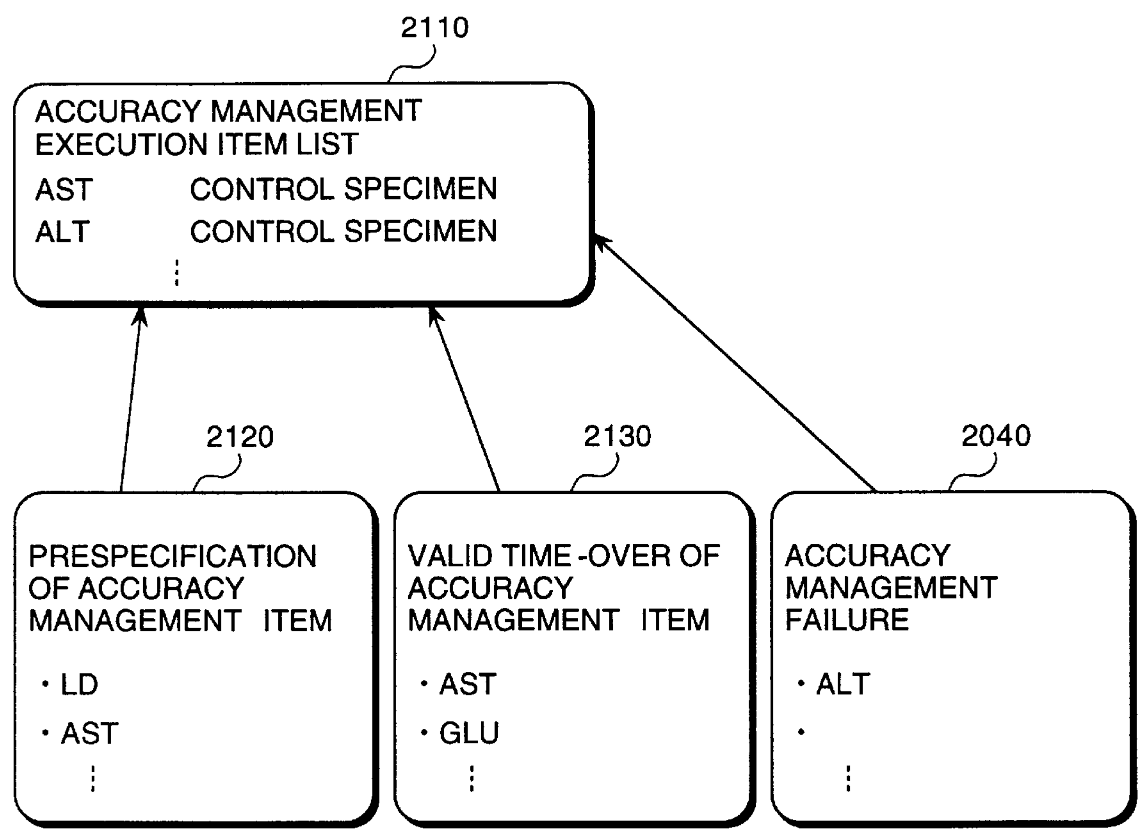
FIG. 21 is a drawing for explaining the mutual relationship of data to be stored by the support system of the present invention.

FIG. 21 shows the mutual relationship of data on accuracy management which occurs in correspondence with the operation of the aforementioned support system and is stored in the storage part 45.

Firstly, a first example of the aforementioned mutual relationship of data will be shown.

As preset data 2120 of an accuracy management item, an analysis item whose accuracy management is stationarily executed is preset by an operator. As reliable time-over data 2130 of an accuracy management item, an analysis item whose accuracy management is re-executed is preset by an operator when the accuracy management reliable time elapses. As accuracy management failure data 2140, an analysis item whose accuracy management is re-executed is preset by an operator when the accuracy management fails.

When the automatic analyzer is in the state of executing the accuracy management to be executed stationarily, this support system reads the preset data 2120 of an accuracy management item, generates an accuracy management execution item list 2110 storing the analysis item for which accuracy management is to be executed and the control sample in correspondence with each other by referring to the accuracy management information 1910 (see FIG. 19) regarding the analysis item which is set as preset data 2120 of an accuracy management item, and executes accuracy management on the basis of the accuracy management execution item list 2110.

When an accuracy management whose reliable time has elapsed, this support system decides whether the analysis item of this accuracy management is set as reliable time-over data 2130 of an accuracy management item or not. When it is decided that the analysis item of this accuracy management is set as reliable time-over data 2130 of an accuracy management item, the support system generates an accuracy management execution item list 2110 storing the analysis item for which accuracy management is to be executed and the control sample in correspondence with each other by referring to the calibration information 1900 (see FIG. 19) regarding the analysis item, and executes accuracy management on the basis of the accuracy management execution item list 2110. When it is decided that the analysis item of this accuracy management is not set as reliable time-over data 2130 of an accuracy management item, the support system will not generate an accuracy management execution item list 2110.

When the accuracy management fails, this support system decides whether the analysis item of this accuracy management is set as accuracy management failure data 2140 or not. When it is decided that the analysis item of this accuracy management is set as accuracy management failure data 2140, the support system generates an accuracy management execution item list 2110 storing the analysis item for which accuracy management is to be executed and the control sample in correspondence with each other by referring to the accuracy management information 1910 (see FIG. 19) regarding the analysis, item and executes accuracy management on the basis of the accuracy management execution item list 2110. When it is decided that the analysis item of this accuracy management is not set as accuracy management failure data 2140, the support system will not generate an accuracy management execution item list 2110.

Next, a second example of the mutual relationship of data on accuracy management will be shown.

As preset data 2120 of an accuracy management item, the Pre-Setting item received at Step 1010 of the accuracy management presetting process shown in FIG. 10 is stored. The reliable time-over data 2130 of an accuracy management item is the Time-Over item stored at Step 1410 of the accuracy management reliable time-over recovery process shown in FIG. 14. The accuracy management failure data 2140 is the QC Failed item stored at Step 1210 of the accuracy management failure recovery process shown in FIG. 12. When these preset data 2120 of an accuracy management item, reliable time-over data 2130 of an accuracy management item, and accuracy management failure data 2140 occur, the total control computer 40 generates an accuracy management execution item list 2110 storing the analysis item for which accuracy management is to be executed and the control sample in correspondence with each other by referring to the accuracy management information 1910 and executes accuracy management on the basis of the accuracy management execution item list 2110.

Furthermore, the total control computer 40 stores the reference sample name, reference sample rack number, reference sample container position in the reference sample rack, reference sample identification information (ID), and reference sample lot number in correspondence with each other. When a calibration to be executed occurs, it is possible to display the reference sample name, reference sample rack number, reference sample container position in the reference sample rack, reference sample identification information (ID), and reference sample lot number which are necessary for this calibration on the display screen of the CRT 43. In the same way, the total control computer 40 stores the control sample name, control sample rack number, control sample container position in the control sample rack, control sample identification information (ID), and control sample lot number in correspondence with each other. When an accuracy management to be executed occurs, it is possible to display the control sample name, control sample rack number, control sample container position in the control sample rack, control sample identification information (ID), and control sample lot number which are necessary for this accuracy management on the display screen of the CRT 43.

An example of such a display screen of the CRT 43 is shown in FIG. 22. In FIG. 22, for example, when a Pre-Setting button 2201 is touched by an operator, the reference sample name necessary for execution of calibration of the preset data 2020 of a calibration item shown in FIG. 20 is displayed in the field of Name 2211, the reference sample rack number in the field of Rack 2212, the reference sample container position in the reference sample rack in the field of Pos 2213, the reference sample identification information (ID) in the field of ID 2214, the reference sample lot number in the field of LOT 2215, and the calibration execution reason in the field of REASON 2216. At the same time, the control sample name necessary for execution of accuracy management of the preset data 2120 of an accuracy management item shown in FIG. 21 is displayed in the field of Name 2217, the control sample rack number in the field of Rack 2218, the control sample container position in the control sample rack in the field of Pos 2219, the control sample identification information (ID) in the field of ID 2220, the control sample lot number in the field of LOT 2221, and the accuracy management execution reason in the field of REASON 2222. When there are many reference samples and control samples whose information is to be displayed, the display screen can be scrolled by the button 2241, button 2242, button 2243, and button 2244.

The automatic analyzer and support system therefor of the present invention can easily inform the analysis item for which calibration or accuracy management is to be performed to an operator for each occurrence cause of necessity via the display screen, and can execute the predetermined calibration or accuracy management accurately for a specific analytical unit in which necessity occurs.

The automatic analyzer of the present invention can transfer a reference sample of an accuracy management sample by the transfer line when necessary, so that a calibration or accuracy management process of an appropriate analysis item can be easily executed repeatedly for an analytical unit among a plurality of arranged analytical units in which necessity is generated.

The automatic analyzer operation method of the present invention can execute calibration or accuracy management easily when a plurality of analytical units are operated efficiently.

We claim:

1. An automatic analyzer support system applied to an automatic analyzer in which a plurality of analytical units are arranged along a transfer line for transferring samples, comprising:

a screen display for displaying a state inspection screen of calibration based on an input request, the state inspection screen having a plurality of state classification captions thereon, said state classification captions including a caption that indicates a state of existence of an analysis item for which a time elapsed since calibration exceeds a predetermined calibration time interval, a caption that indicates a state of existence of an analysis item which has failed calibration, and a caption that indicates a state of existence of an analysis item which relates to a reagent newly added;

a plurality of instruction buttons on said state inspection screen, each of said instruction buttons being provided corresponding to at least one of said state classification captions; and a controller for providing one of said state classification captions with an indication that an analysis item needs to be calibrated according to the state of the indicated caption;

wherein said controller displays, on said state inspection screen, said analysis item needing to be calibrated and information of an analytical unit for the calibration, when said instruction button is selected corresponding to said caption indicated; controls said transfer line so as to transfer a suitable calibrator to said analytical unit for the calibration; and controls said analytical unit so as to measure said calibrator.

2. An automatic analyzer support system according to claim 1, wherein:

said plurality of state classification captions include a caption indicating a state of existence of said analysis item for which said calibration is needed to be executed before said automatic analyzer is operated.

3. An automatic analyzer support system according to claim 1, wherein:

when a state corresponding to one of said plurality of state classification captions occurs, the display state of the corresponding classification caption is changed.

4. An automatic analyzer support system according to claim 1, wherein:

when an occurrence of two or more states requiring calibration for the same analysis item is indicated by two or more state classification captions, the calibration corresponding to one of the two or more state classification captions is executed, and the information by the residual other of the two or more state classification captions is canceled.

5. An automatic analyzer support system applied to an automatic analyzer in which a plurality of analytical units are arranged along a transfer line for transferring samples, comprising:

a screen display for displaying a state inspection screen of accuracy management assessment based on an input request, the state inspection screen having a plurality of state classification captions thereon, said state classification captions including a caption that indicates a state of existence of an analysis item for which an accuracy management assessment is needed before being analyzed by said automatic analyzer, a caption that indicates a state of existence of an analysis item for which a time elapsed since accuracy management assessment exceeds a predetermined accuracy management assessment time interval, and a caption that indicates a state of existence of an analysis item which has failed accuracy management assessment;

a plurality of instruction buttons on said state inspection screen, each of said instruction buttons being provided corresponding to at least one of said state classification captions; and a controller for providing one of said state classification captions with an indication that an accuracy management assessment is needed;

wherein said controller displays, on said state inspection screen, said analysis item needing said accuracy management assessment and information of an analytical unit for the accuracy management assessment, when said instruction button is selected corresponding to said caption indicated; controls said transfer line so as to transfer a suitable control sample to said analytical unit for the accuracy management assessment; and controls said analytical unit so as to measure said control sample.

6. An automatic analyzer support system according to claim 5, wherein:

when a necessity of said accuracy management assessment occurs, said caption relating to a cause for the occurrence flickers.

7. An automatic analyzer support system according to claim 5, wherein:

when an occurrence of two or more states requiring accuracy management assessment for the same analysis item is indicated by two or more state classification captions, accuracy management assessment corresponding to one of the two or more state classification captions is executed, and the information by the residual other of the two or more state classification captions is canceled.

* * * * *